United States Patent
McCabe et al.

(10) Patent No.: US 7,873,413 B2
(45) Date of Patent: Jan. 18, 2011

(54) CLOSED LOOP NEURAL STIMULATION SYNCHRONIZED TO CARDIAC CYCLES

(75) Inventors: Aaron McCabe, Minneapolis, MN (US); Imad Libbus, St. Paul, MN (US); Yi Zhang, Blaine, MN (US); Paul A. Haefner, Circle Pines, MN (US); Alok S. Sathaye, Minneapolis, MN (US); Anthony V. Caparso, St. Louis Park, MN (US); M. Jason Brooke, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 880 days.

(21) Appl. No.: 11/459,481

(22) Filed: Jul. 24, 2006

(65) Prior Publication Data
US 2008/0021504 A1 Jan. 24, 2008

(51) Int. Cl.
*A61N 1/36* (2006.01)
(52) U.S. Cl. .............................. 607/9; 607/7
(58) Field of Classification Search .............. 607/7, 607/9
See application file for complete search history.

(56) References Cited
U.S. PATENT DOCUMENTS

| | | |
|---|---|---|
| 3,650,277 A | 3/1972 | Sjostrand et al. |
| 5,203,326 A | 4/1993 | Collins |
| 5,318,592 A | 6/1994 | Schaldach |
| 5,356,425 A | 10/1994 | Bardy et al. |
| 5,411,531 A | 5/1995 | Hill et al. |
| 5,507,784 A | 4/1996 | Hill et al. |
| 5,522,854 A | 6/1996 | Ideker et al. |
| 5,916,239 A | 6/1999 | Geddes et al. |
| 5,928,272 A | 7/1999 | Adkins et al. |
| 6,006,134 A | 12/1999 | Hill et al. |
| 6,415,183 B1 | 7/2002 | Scheiner et al. |
| 6,522,926 B1 | 2/2003 | Kieval et al. |
| 6,564,096 B2 | 5/2003 | Mest |
| 6,622,041 B2 * | 9/2003 | Terry et al. ............... 607/9 |
| 7,123,961 B1 | 10/2006 | Kroll et al. |
| 7,155,278 B2 * | 12/2006 | King et al. ............... 607/2 |
| 7,542,800 B2 | 6/2009 | Libbus et al. |
| 2002/0026221 A1 | 2/2002 | Hill et al. |
| 2002/0026222 A1 | 2/2002 | Schauerte et al. |
| 2002/0107553 A1 | 8/2002 | Hill et al. |

(Continued)

FOREIGN PATENT DOCUMENTS
WO  WO-2006044025 A1  4/2006

OTHER PUBLICATIONS

"U.S. Appl. No. 11/099,141, Final Office Action mailed Oct. 22, 2007", 10 pgs.

(Continued)

*Primary Examiner*—Carl H Layno
*Assistant Examiner*—Deborah Malamud
(74) *Attorney, Agent, or Firm*—Schwegman, Lundberg & Woessner, P.A.

(57) ABSTRACT

Various aspects of the present subject matter relate to a method. According to various method embodiments, cardiac activity is detected, and neural stimulation is synchronized with a reference event in the detected cardiac activity. Neural stimulation is titrated based on a detected response to the neural stimulation. Other aspects and embodiments are provided herein.

29 Claims, 13 Drawing Sheets

U.S. PATENT DOCUMENTS

| | | | |
|---|---|---|---|
| 2002/0120304 | A1 | 8/2002 | Mest |
| 2002/0165586 | A1 | 11/2002 | Hill et al. |
| 2003/0078623 | A1 | 4/2003 | Weinberg et al. |
| 2003/0100924 | A1 | 5/2003 | Foreman et al. |
| 2004/0193231 | A1 | 9/2004 | David et al. |
| 2004/0210261 | A1* | 10/2004 | King et al. .................... 607/9 |
| 2005/0096705 | A1 | 5/2005 | Pastore et al. |
| 2005/0143779 | A1 | 6/2005 | Libbus |
| 2005/0143785 | A1 | 6/2005 | Libbus |
| 2005/0148896 | A1 | 7/2005 | Siejko et al. |
| 2005/0149126 | A1 | 7/2005 | Libbus |
| 2005/0149127 | A1 | 7/2005 | Libbus |
| 2005/0149128 | A1 | 7/2005 | Heil, Jr. et al. |
| 2005/0149129 | A1 | 7/2005 | Libbus et al. |
| 2005/0149130 | A1 | 7/2005 | Libbus |
| 2005/0149131 | A1 | 7/2005 | Libbus et al. |
| 2005/0149132 | A1 | 7/2005 | Libbus |
| 2005/0149133 | A1 | 7/2005 | Libbus et al. |
| 2005/0149143 | A1 | 7/2005 | Libbus et al. |
| 2005/0149155 | A1 | 7/2005 | Scheiner et al. |
| 2005/0149156 | A1 | 7/2005 | Libbus et al. |
| 2005/0197674 | A1 | 9/2005 | McCabe et al. |
| 2005/0261741 | A1 | 11/2005 | Libbus et al. |
| 2006/0079945 | A1 | 4/2006 | Libbus |
| 2006/0106429 | A1 | 5/2006 | Libbus et al. |
| 2006/0116737 | A1 | 6/2006 | Libbus |
| 2006/0122675 | A1 | 6/2006 | Libbus et al. |
| 2006/0206154 | A1 | 9/2006 | Moffitt et al. |
| 2006/0217772 | A1 | 9/2006 | Libbus et al. |
| 2006/0224188 | A1 | 10/2006 | Libbus et al. |
| 2008/0167693 | A1 | 7/2008 | Kieval et al. |
| 2009/0228060 | A1 | 9/2009 | Libbus et al. |

OTHER PUBLICATIONS

"U.S. Appl. No. 11/099,141, Non-Final Office Action mailed May 6, 2008", 11 pgs.

"U.S. Appl. No. 11/099,141, Response filed Jan. 6, 2009 to Final Final Office Action mailed Nov. 7, 2008", 9 pgs.

"U.S. Appl. No. 11/099,141, Response filed Feb. 19, 2008 to Final Office Action mailed Oct. 22, 2007", 13 pgs.

"U.S. Appl. No. 11/099,141, Response filed Apr. 5, 2007 to Restriction Requirement mailed Mar. 6, 2007", 11 pgs.

"U.S. Appl. No. 11/099,141, Response filed Aug. 4, 2008 to Non Final Office Action mailed May 6, 2008", 10 pgs.

"U.S. Appl. No. 11/099,141, Restriction Requirement mailed Mar. 6, 2007", 6 pgs.

"U.S. Appl. No. 11/099,141, Final Office Action mailed Nov. 7, 2008", 8 pgs.

"U.S. Appl. No. 11/099,141 Non Final Office Action mailed May 18, 2007", 9 pgs.

"U.S. Appl. No. 11/099,141 Response filed Aug. 20, 2007 to Non Final Office Action mailed May 18, 2007", 11 pgs.

"U.S. Appl. No. 11/868,408, Preliminary Amendment filed Oct. 5, 2007", 2 pgs.

Chapleau, Mark W., "Contrasting effects of static and pulsatile pressure on carotid baroreceptor activity in dogs", *Circulation*, vol. 61, No. 5, (Nov. 1987), 648-658.

Chapleau, Mark W., "Pulsatile activation of baroreceptors causes central facilitation of baroreflex", *American Journal Physiol Heart Circ Physiol*, (Jun. 1989), 256: H1735-1741.

Coleridge, J. C., et al., "Relationship between pulmonary arterial pressure and impulse activity in pulmonary arterial baroreceptor fibres", *Journal of Physiology*, (Sep. 1961), 197-205.

Coleridge, J. C., "The distribution, connexions and history of baroreceptors in the pulmonary artery, with some observations on the sensory innervation of the ductus arteriosus", *Journal of Physiology*, 156, (May 1961), 591-602.

Levy, M. N., "Effects of repetitive bursts of vagal activity on heart rate.", *Circulation Research*, 30 (2), (Feb. 1972), 186-95.

Martin, P., "Time-dependent heart period and contractility responses to successive brief vagal stimuli", *Am J Physiol*, 239(4), (Oct. 1980), H494-H500.

Sigurdsson, Axel, "The role of neurohormonal activation in chronic heart failure and postmyocardial infarction", *American Heart Journal*, 132 (1 Pt 2 Su), (Jul. 1996), 229-234.

"U.S. Appl. No. 11/099,141, Notice of Allowance mailed Jan. 28, 2009", 4 pgs.

\* cited by examiner

CLOSED LOOP NEURAL STIMULATION SYNCHRONIZED TO CARDIAC CYCLES

FIELD

This application relates generally to medical devices and, more particularly, to systems, devices and methods for providing neural stimulation.

BACKGROUND

The heart is the center of a person's circulatory system. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. These pumping functions are accomplished by cyclic contractions of the myocardium (heart muscles). Each cycle, known as the cardiac cycle, includes systole and diastole. During systole, the heart ejects blood. During diastole, the heart is filled with blood for the next ejection (systolic) phase, and the myocardial tissue is perfused. In a normal heart, the sinoatrial node generates electrical impulses called action potentials. The electrical impulses propagate through an electrical conduction system to various regions of the heart to excite the myocardial tissue of these regions. Coordinated delays in the propagations of the action potentials in a normal electrical conduction system cause the various portions of the heart to contract in synchrony to result in efficient pumping functions indicated by a normal hemodynamic performance. A blocked or otherwise abnormal electrical conduction and/or deteriorated myocardial tissue result in systolic dysfunction—because the myocytes do not contract in unison—and diastolic dysfunction—because the myocytes do not relax in unison. Decreased systolic and diastolic performance each contribute to a poor overall hemodynamic performance, including a diminished blood supply to the heart and the rest of the body.

The hemodynamic performance is modulated by neural signals in portions of the autonomic nervous system. For example, the myocardium is innervated with sympathetic and parasympathetic nerves. Activities in these nerves modulate the heart rate and contractility (strength of the myocardial contractions). Stimulation applied to the sympathetic nerves is known to increase the heart rate and the contractility, shortening the systolic phase of a cardiac cycle, and lengthening the diastolic phase of the cardiac cycle. Stimulation applied to the parasympathetic nerves is known to have essentially the opposite effects.

It has been proposed to stimulate the autonomic nerves to treat abnormal cardiac conditions, such as to control myocardial remodeling and to prevent arrhythmias following myocardial infarction. During heart failure, reduced autonomic balance (increase in sympathetic and decrease in parasympathetic cardiac tone) has been shown to be associated with left ventricular dysfunction and increased mortality. Data further indicate that increasing parasympathetic tone and reducing sympathetic tone may beneficially protect the myocardium from further remodeling and predisposition to fatal arrhythmias following myocardial infarction. It is observed that the effects of autonomic stimulation are dependent on timing of the delivery of electrical stimuli in relation to the cardiac cycle.

SUMMARY

Various aspects of the present subject matter relate to a system. Various system embodiments comprise a reference event detection circuit, a feedback detection circuit, a stimulation control circuit, and a stimulation output circuit. The reference event detection circuit is adapted to receive an input from a reference signal sensor and generate a synchronization control signal using a detected cardiac activity event. The feedback detection circuit is adapted to receive an input from a feedback sensor and generate a feedback control signal. The stimulation control circuit is adapted to generate a stimulation control signal. The stimulation control circuit includes a synchronization circuit responsive to the synchronization control signal to time the stimulation control signal, and a therapy titration circuit responsive to the feedback control signal to adjust the stimulation control signal. The stimulation output circuit is responsive to the stimulation control signal from the stimulation control circuit and is adapted to generate a neural stimulation signal for use in stimulating at least one autonomic neural target. The neural target(s) can include one, two or more neural targets to produce a desired response such as a desired change in heart rate, PR interval and the like.

Various system embodiments comprise a heart rate detector, a feedback detection circuit, a stimulation control circuit, and a stimulation output circuit. The heart rate detector is adapted to generate a synchronization control signal using a detected heart rate. The feedback detection circuit is adapted to receive an input from a cardiac data sensor and generate a feedback control signal using detected cardiac data. The stimulation control circuit is adapted to generate a stimulation control signal, and includes a synchronization circuit responsive to the synchronization control signal to time the stimulation control signal and a therapy titration circuit responsive to the feedback control signal to adjust the stimulation control signal. The stimulation output circuit is responsive to the stimulation control signal from the stimulation control circuit and is adapted to generate a neural stimulation signal for use in stimulating an autonomic neural target.

Various aspects of the present subject matter relate to a method. According to various method embodiments, cardiac activity is detected, and neural stimulation is synchronized with a reference event in the detected cardiac activity. Neural stimulation is titrated based on a detected response to the neural stimulation.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1:
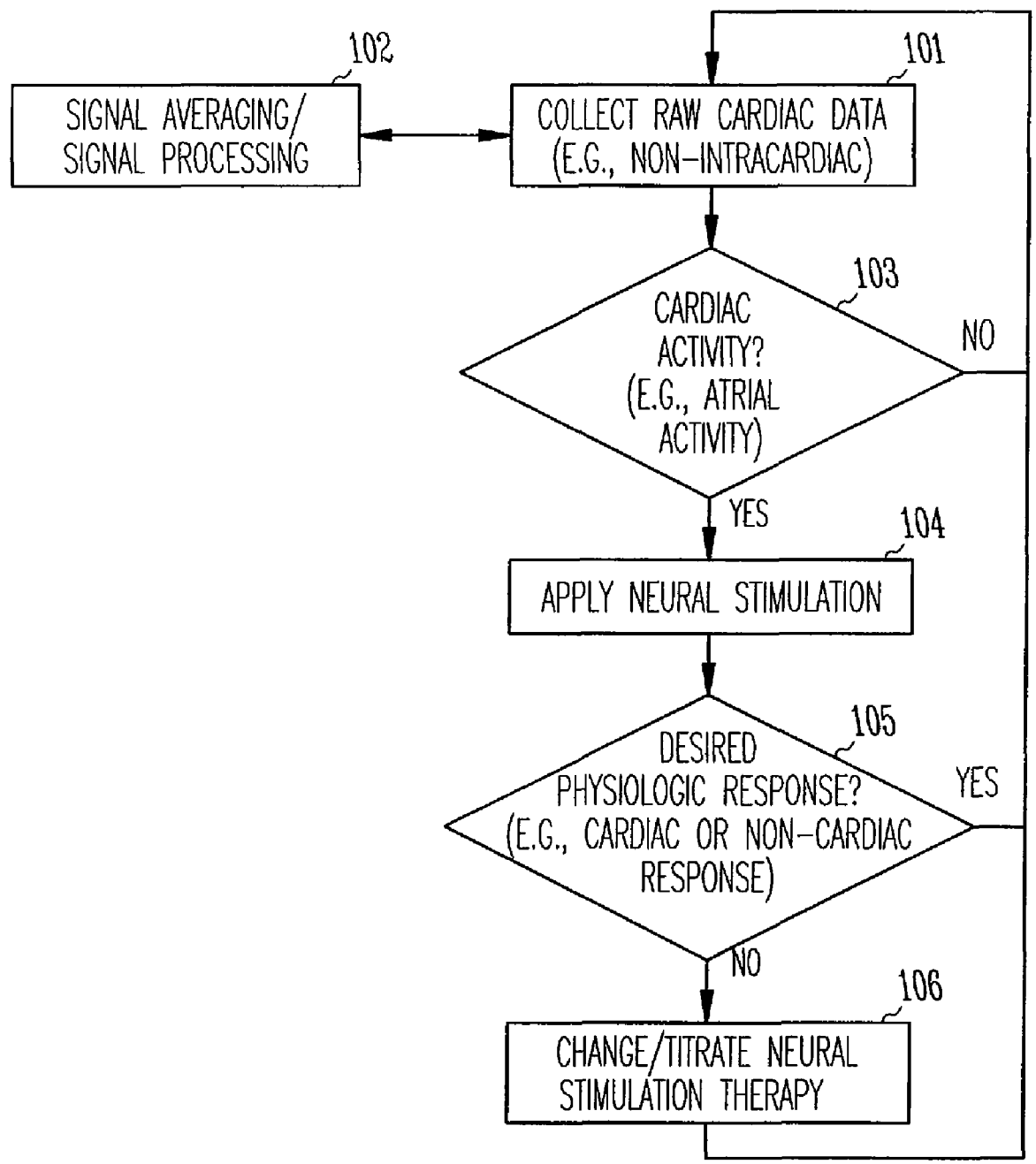
FIG. 1 illustrates a neural stimulation method, according to various embodiments.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter may be used in any cardiac device which has neural stimulation capabilities, or in any neural stimulation device for cardiac applications. Various embodiments include an implantable device, and various embodiments includes an external device. The therapy may be of significant benefit in post myocardial infarction (post MI) and heart failure (HF) patients, or in patients with other cardiovascular conditions (e.g. hypertension, syncope, etc.).

Embodiments of the present subject matter synchronize neural stimulation to the cardiac cycle (such as is disclosed in U.S. application Ser. No. 11/099,141, entitled "Method and Apparatus For Synchronizing Neural Stimulation to Cardiac Cycles," filed Apr. 5, 2005 and incorporated by reference in its entirety) and further provide stimulation feedback using a physiologic response to the neural stimulation (e.g. a cardiac response such as a detected heart rate or a non-cardiac response such as respiration). For example, while the nervous system is stimulated to evoke a sympathetic response (sympathetic stimulation and/or parasympathetic inhibition) to increase the heart rate, a system embodiment triggers the pulses based on ECG alignment and also monitors the change in heart rate. If the heart rate response is not as expected or desired, a new stimulation waveform, site and/or vector is chosen until the appropriate increased heart rate is achieved. Likewise, a similar method can be applied to neural stimulation to evoke a parasympathetic response (parasympathetic stimulation and/or sympathetic inhibition) to decrease the heart rate.

Closed loop systems allow chronic changes in the response to neural stimulation to be mitigated, allow the response (e.g. rate of change) to be controlled by observing and selecting different stimulation waveforms, sites, and vectors for different desired rates, provide fully automatic neural stimulation device free from physician intervention if disease or other chronic affects change the neural response, and allow the device therapy response to be tailored or a specific patient and/or implant.

Some embodiments include a device capable of stimulating neural targets and monitoring ECG signals that is programmed to titrate therapy based on heart rate (steady heart rate or a heart rate increase or decrease based on a percentage value or beats per minute or other means for quantifying the increase or decrease). Other metrics from the ECG (AV delay, T-wave velocity, etc.) can be used to provide cardiac activity feedback. According to various embodiments, titrating the therapy intensity includes changing a signal feature (e.g. amplitude, pulse duration, frequency, and/or waveform), neural target site (via multiple electrodes), and/or vector (via the same or different vectors). Various embodiments perform an iterative process where a stimulation is changed and the resulting cardiac activity is monitored. If appropriate after a designated time course or predetermined event (e.g. the therapy is not providing the desired cardiac activity response) the device will precede to the next permutation of therapy.

FIG. 1 illustrates a neural stimulation method, according various embodiments. Raw cardiac data is collected at 101. In various embodiments, the cardiac data includes non-intracardiac data, such as may be collected by an ECG signal or a P-wave or R wave detector, for example. In various embodiments, the cardiac data includes sensed electrical activity by cardiac leads. The raw data can be averaged or otherwise processed at 102. At 103, it is determined whether cardiac activity has occurred. The detected cardiac activity triggers (with or without a delay) neural stimulation at 104 such that the neural stimulation is synchronized to the cardiac activity. At 105, it is determined whether the resulting cardiac activity or non-cardiac effects are desired. If the resulting cardiac activity or non-cardiac effects are not expected, the process proceeds to 106 to change or titrate the neural stimulation therapy. Various embodiments titrate therapy by increasing the intensity of the therapy or decreasing the intensity of therapy. Various embodiments titrate therapy by changing a feature of the neural stimulation signal (e.g. amplitude, frequency, pulse duration and/or waveform). Various embodiments titrate therapy by changing a stimulation vector which changes the neural stimulation. Some embodiments change the vector to change between stimulating neural traffic and inhibiting neural traffic. Various embodiments titrate therapy by changing the electrodes used to provide the electrical therapy. Thus, given N electrodes, the therapy can change from using a first set of electrodes selected from the N electrodes to a second set of electrodes selected from the N electrodes. An electrode can be in one set but not the other, or can be in both sets. Some sets only include electrodes that are not in the other set.

Figure 2:
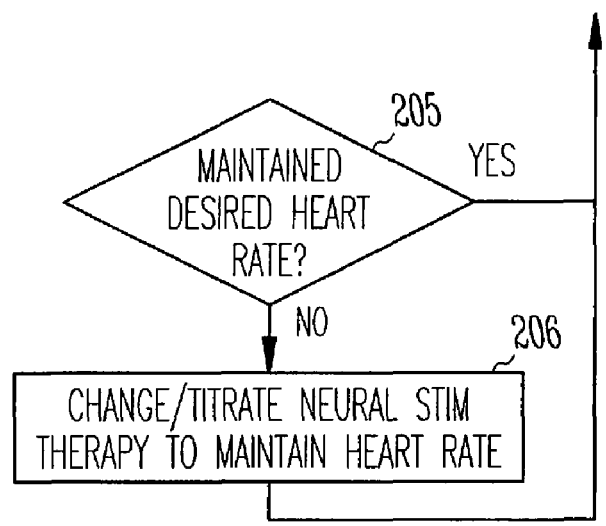
FIG. 2 illustrates a neural stimulation titration method to maintain heart rate, according to various embodiments.

FIG. 2 illustrates a neural stimulation titration method to maintain heart rate, according to various embodiments. Other physiologic responses can be used in place of or in addition to heart rate. The illustrated process generally corresponds to determining if the resulting cardiac activity or non-cardiac effects are desired and titrating the neural stimulation accordingly, as illustrated in FIG. 1. At 205, it is determined whether the desired heart rate (e.g. range of acceptable heart rates) has been maintained. If the heart rate has not been maintained, the process proceeds to 206 to change or titrate the neural stimulation therapy to maintain the heart rate.

Figure 3:
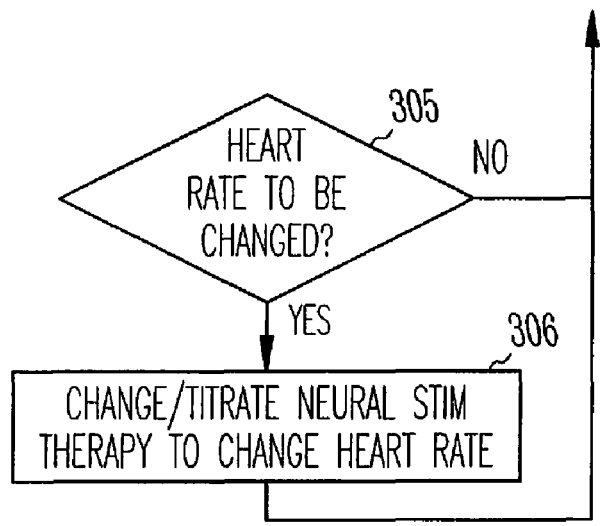
FIG. 3 illustrates a neural stimulation titration method to change a heart rate, according to various embodiments.

FIG. 3 illustrates a neural stimulation titration method to change a heart rate, according to various embodiments. Other physiologic responses can be used in place of or in addition to heart rate. The illustrated process generally corresponds to determining if the resulting cardiac activity or non-cardiac effects are desired and titrating the neural stimulation accordingly, as illustrated in FIG. 1. At 305, it is determined whether the heart rate is to be changed (e.g. percentage or change in beats per minute). If the heart rate is to be changed, the process proceeds to 306 to change or titrate the neural stimulation therapy to change the heart rate as desired.

Various neural stimulation system embodiments include an implantable neural stimulator that senses a reference signal indicative of cardiac cycles each including a predetermined type timing reference event using an implantable reference event sensor. Various embodiments use an intracardiac lead to detect the reference event. In an embodiment, the implantable reference event sensor is an extracardiac and extravascular sensor, i.e., a sensor that is placed external to a patient's circulatory system including the heart and blood vessels. The delivery of the neural stimulation pulses are synchronized to the timing reference event. Examples of the reference signal include a wireless ECG, an acoustic signal indicative of heart sounds, and a hemodynamic signal. For example, the reference event can be a directly detected P-wave or a P-wave derived using a detected QRS signal, signal averaging Doppler flow, and acoustic signals.

In this document, "ECG" includes surface ECG, wireless ECG and subcutaneous ECG. In this document, "Surface ECG" refers to a cardiac electrical signal sensed with electrodes attached onto the exterior surface of the skin. "Wireless ECG" refers to a signal approximating the surface ECG, acquired without using surface (non-implantable, skin contact) electrodes. "Subcutaneous ECG" is a form of wireless ECG and includes a cardiac electrical signal sensed through electrodes implanted in subcutaneous tissue, such as through electrodes incorporated onto an implantable medical device that is subcutaneously implanted. As reflected in their corresponding morphologies, the surface ECG results from electrical activities of the entire heart. The wireless ECG, including but not being limited to the subcutaneous ECG, has a morphology that approximates that of the surface ECG and reflects electrical activities of a substantial portion of the heart, up to the entire heart.

In this document, an "acoustic signal" includes any signal indicative of heart sounds. "Heart sounds" include audible mechanical vibrations caused by cardiac activity that can be sensed with a microphone and audible and inaudible mechanical vibrations caused by cardiac activity that can be sensed with an accelerometer. Known type heart sounds include the "first heart sound" or S1, the "second heart sound" or S2, the "third heart sound" or S3, the "fourth heart sound" or S4, and their various sub-components. S1 is known to be indicative of, among other things, mitral valve closure, tricuspid valve closure, and aortic valve opening. S2 is known to be indicative of, among other things, aortic valve closure and pulmonary valve closure. S3 is known to be a ventricular diastolic filling sound often indicative of certain pathological conditions including heart failure. S4 is known to be a ventricular diastolic filling sound resulted from atrial contraction and is usually indicative of pathological conditions. The term "heart sound" hereinafter refers to any heart sound (e.g., S1) and any components thereof (e.g., M1 component of S1, indicative of Mitral valve closure).

In this document, a "hemodynamic signal" includes a signal providing for monitoring, calculation, or estimation of one or more measures of hemodynamic performance such as blood pressure or pressure-related parameters, cardiac output, stroke volume, volume of blood flow, change in (e.g., derivative of) the volume of blood flow, and/or velocity of blood flow.

Various embodiments titrate therapy based on a change in heart rate, such as a percentage change or a quantitative change such as beats per minute, or based on other measurable cardiac effects. Examples of ECG-derived parameters include heart rate variability (HRV), heart rate turbulence (HRT), AV delay, and T-wave velocity. Heart sound waveforms may be used, as well as changes in photoplethysmography, and non-cardiac effects such as respiration and blood pressure. The therapy is titrated by means for a changeable stimulation methodology via waveform modulation, site or vector changes.

Figure 4:
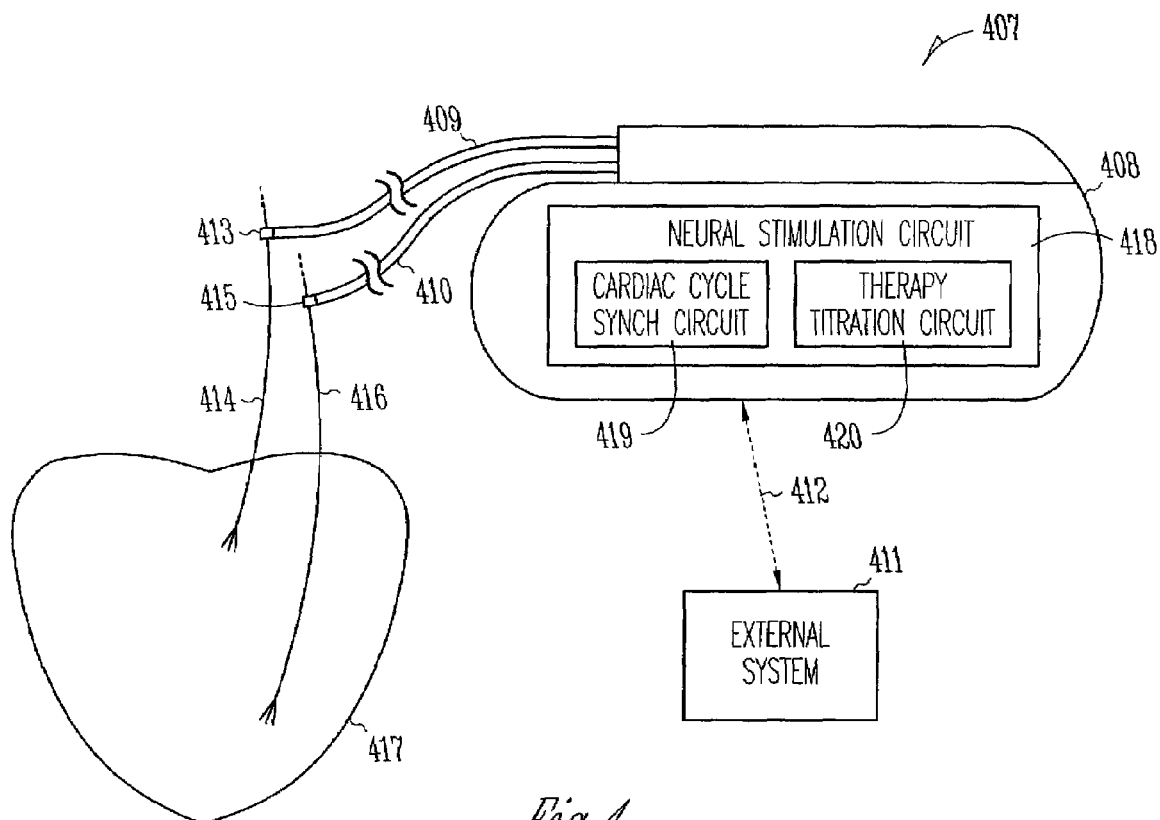
FIG. 4 is an illustration of an embodiment of a neural stimulation system and portions of an environment in which system is used.

FIG. 4 is an illustration of an embodiment of a neural stimulation system 407 and portions of an environment in which system 407 is used. System 407 includes implantable medical device 408 that delivers neural stimulation pulses through leads 409 and 410, an external system 411, and a telemetry link 412 providing for communication between implantable medical device 408 and external system 411. For illustrative purpose only, FIG. 4 shows that lead 409 includes an electrode 413 coupled to a nerve 414 of the sympathetic nervous system, and lead 410 includes an electrode 415 coupled a nerve 416 of the parasympathetic nervous system. Neural targets can be stimulated using nerve cuffs, intravascularly-fed electrodes positioned to transvascularly stimulate the neural targets, and stimulation electrodes wirelessly connected to the system. Neural targets may also be stimulated using non-electrical energy, such as may be produced by transducers that provide ultrasonic, light and magnetic energy. Nerves 414 and 416 innervate a heart 417. In various embodiments, implantable medical device 408 provides neural stimulation to any one or more nerves through one or more leads for modulating one or more functions of the circulatory system including heart 417. Such leads include implantable neural leads each including at least one electrode for sensing neural activities and/or delivering neural stimulation pulses. One example of such an electrode includes a cuff electrode for placement around an aortic, carotid, or vagus nerve. An embodiment includes an intravascularly-placed electrode positioned in an internal jugular vein (IJV) to stimulate a vagus nerve, or in an aorta or pulmonary artery positioned to stimulate neural targets proximate thereto.

Implantable medical device 408 delivers the neural stimulation pulses and includes a neural stimulation circuit 418. The illustrated neural stimulation circuit 418 includes a cardiac cycle synchronization circuit 419, a therapy titration circuit 420 which receives resulting cardiac activity feedback which can be representative of the efficacy of the therapy. Neural stimulation circuit 418 detects a predetermined type timing reference event from a cardiac cycle and synchronizes the delivery of neural stimulation pulses to that timing reference event. In one embodiment, neural stimulation circuit 418 starts a predetermined offset time interval upon detection of the timing reference event and delivers a burst of neural stimulation pulses when the offset time interval expires. In one embodiment, implantable medical device 408 is capable of monitoring physiologic signals and/or delivering therapies in addition to the neural stimulation. Examples of such additional therapies include cardiac pacing therapy, cardioversion/defibrillation therapy, cardiac resynchronization therapy, cardiac remodeling control therapy, drug therapy, cell therapy, and gene therapy. In various embodiments, implantable medical device 408 delivers the neural stimulation in coordination with one or more such additional therapies.

External system 411 provides for control of and communication with implantable medical device 408 by a physician or other caregiver. In one embodiment, external system 411 includes a programmer. In another embodiment, external system 411 is a patient management system including an external device communicating with implantable medical device 408 via telemetry link 412, a remote device in a relatively distant location, and a telecommunication network linking the external device and the remote device. The patient management system allows access to implantable medical device 408 from a remote location, for purposes such as monitoring patient status and adjusting therapies. In one embodiment, telemetry link 412 is an inductive telemetry link. In an embodiment, telemetry link 412 is a far-field radio-frequency (RF) telemetry link. Telemetry link 412 provides for data transmission from implantable medical device 408 to external system 411. This includes, for example, transmitting real-time physiological data acquired by implantable medical device 408, extracting physiological data acquired by and stored in implantable medical device 408, extracting patient history data such as occurrences of arrhythmias and therapy deliveries recorded in implantable medical device 408, and/or extracting data indicating an operational status of implantable medical device 408 (e.g., battery status and lead impedance). Telemetry link 412 also provides for data transmission from external system 411 to implantable medical device 408. This includes, for example, programming implantable medical device 408 to acquire physiological data, programming implantable medical device 408 to perform at least one self-diagnostic test (such as for a device operational status), and/or programming implantable medical device 408 to deliver one or more therapies and/or to adjust the delivery of one or more therapies.

Figure 5:
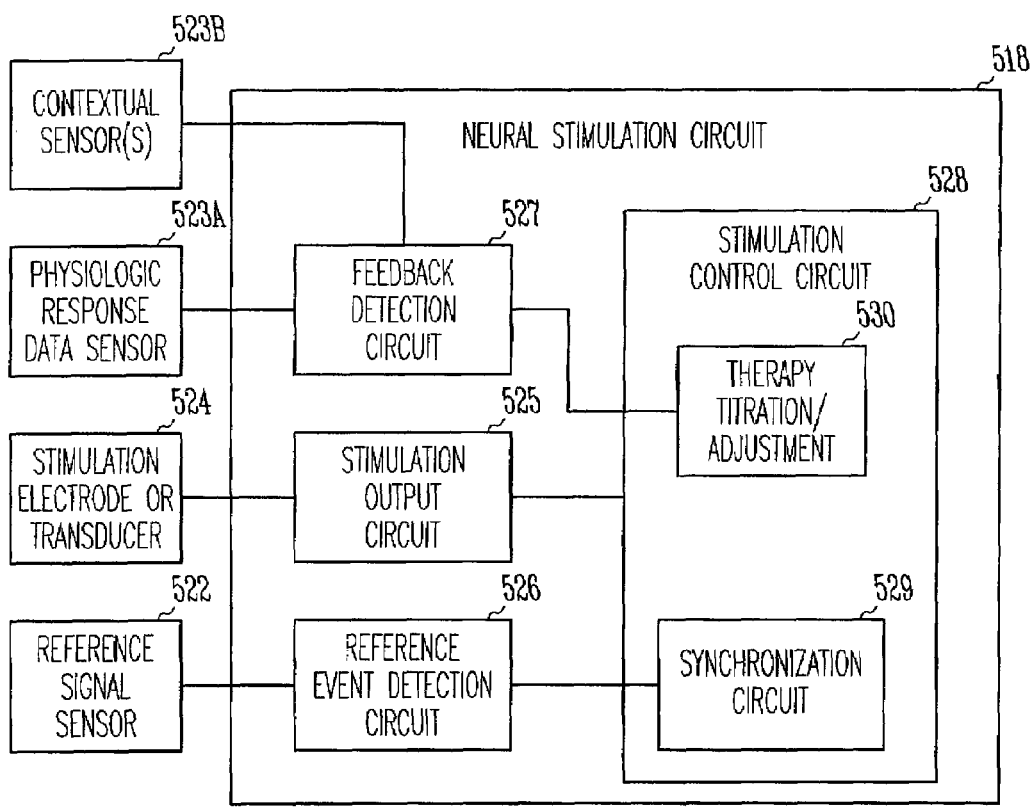
FIG. 5 is a block diagram illustrating an embodiment of a circuit of a neural stimulation system.

FIG. 5 is a block diagram illustrating an embodiment of a circuit of a neural stimulation system 521. System 521 includes a reference signal sensor 522, a data sensor 523A adapted to sense a physiologic response to the neural stimulation, a stimulation electrode/transducer 524, and a neural stimulation circuit 518. Reference signal sensor 522 senses a reference signal indicative of cardiac cycles each including a predetermined type timing reference event. In one embodiment, reference signal sensor 522 is an implantable reference signal sensor. The timing reference event is a recurring feature of the cardiac cycle that is chosen to be a timing reference to which the neural stimulation is synchronized. In an embodiment, reference signal sensor 522 includes an electrode in or near the heart, such as may be incorporated in an intracardiac lead. In one embodiment, reference signal sensor 522 is configured for extracardiac and extravascular placement, i.e., placement external to the heart and blood vessels. Examples of reference signal sensor 522 include a set of electrodes for sensing a subcutaneous ECG signal, an acoustic sensor for sensing an acoustic signal indicative of heart sounds, and a hemodynamic sensor for sensing a hemodynamic signal indicative of hemodynamic performance. In one embodiment, an implantable medical device has an implantable housing that contains both a reference signal sensor 522 and neural stimulation circuit 518. In an embodiment, reference signal sensor 522 is incorporated onto the housing of an implantable medical device. In another embodiment, reference signal sensor 522 is electrically connected to an implantable medical device through one or more leads. In another embodiment, reference signal sensor 522 is communicatively coupled to an implantable medical device via an intra-body telemetry link.

Neural stimulation circuit 518 includes a stimulation output circuit 525, a reference event detection circuit 526, a feedback detection circuit 527, and a stimulation control circuit 528. Reference event detection circuit 526 receives the reference signal from reference signal sensor 522 and detects the timing reference event from the reference signal. Stimulation control circuit 528 controls the delivery of the neural stimulation pulses and includes a synchronization circuit or module 529 and a therapy titration adjustment circuit or module 530. Synchronization module 529 receives a signal indicative of the detection of each timing reference event and synchronizes the delivery of the neural stimulation pulses to the detected timing reference event. Stimulation output circuit 525 delivers neural stimulation pulses upon receiving a pulse delivery signal from stimulation control circuit 528. Data sensor 523A provides signals indicative of a physiological response to the applied neural stimulation. A feedback detection circuit 527 receives the signal indicative of the response and processes the signal to provide a neural stimulation feedback signal. In various embodiments, the response includes a cardiac activity such as heart rate, HRV, HRT, PR interval, T-wave velocity, or action potential duration. In various embodiments the response includes a non-cardiac response such as respiration or blood pressure. In various embodiments, the response includes a QT interval or atrial/ventricular refractory periods. The therapy titration/adjustment module 530 uses the feedback signal to modulate or titrate the therapy generated by the stimulation output circuit 525 to provide the desired physiologic response (e.g. cardiac response or non-cardiac response). Contextual sensor(s) or input(s) 523B are also illustrated connected to the feedback detection circuit 527 to provide a more complete picture of a patient's physiology. The feedback detection circuit can provide the neural stimulation feedback signal based on the sensor 523A and the contextual input(s) 523B. The contextual input(s) can be used to avoid incomplete data from affecting the neural stimulation. Examples of contextual inputs include an activity sensor, a posture sensor and a timer. Any one or combination of two or more contextual inputs can be used by the feedback detection circuit. For example, an elevated heart rate may be representative of exercise rather than a reason for titrating the neural stimulation therapy.

Figure 6:
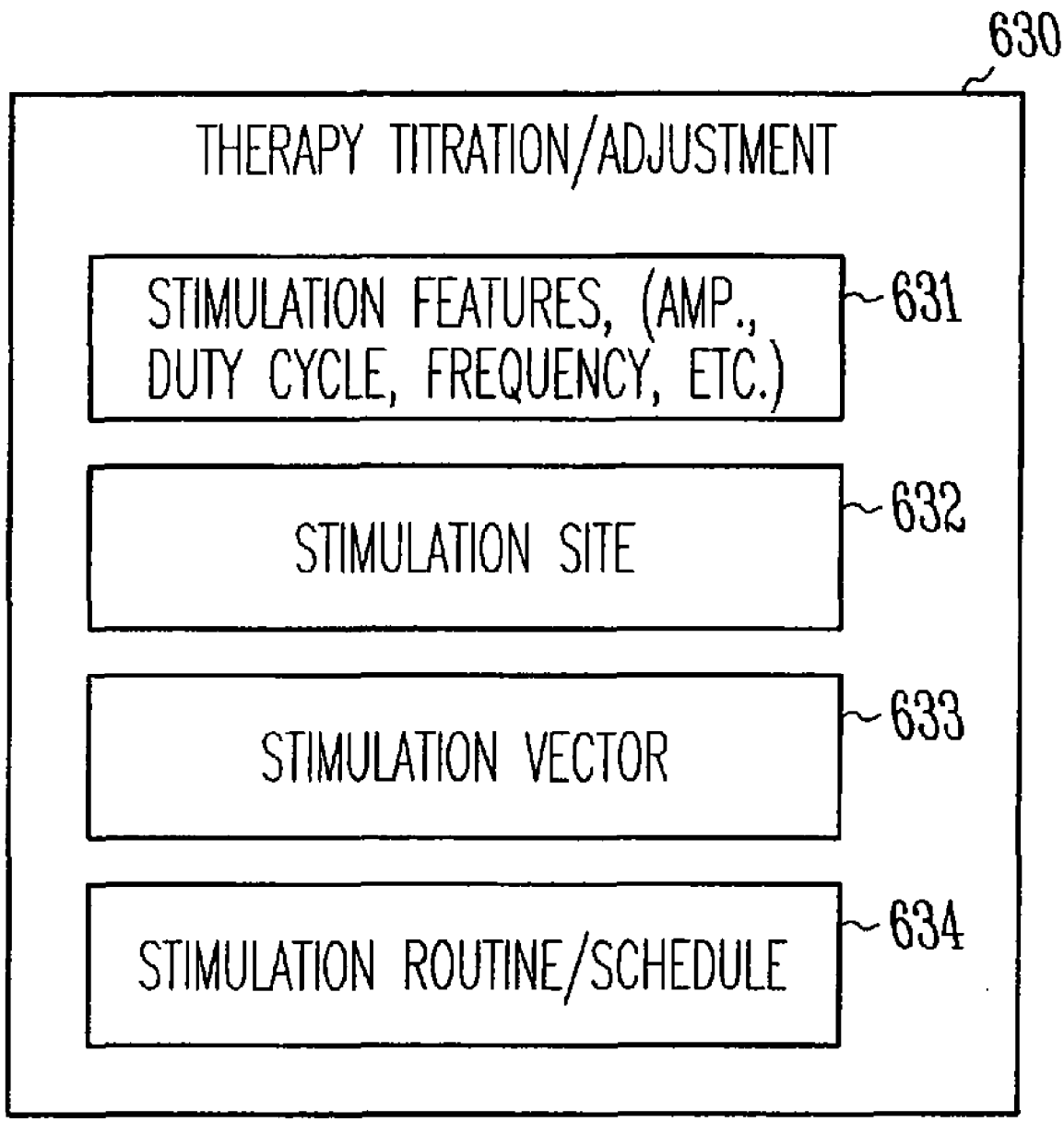
FIG. 6 illustrates an embodiment of a therapy titration module such as is illustrated in FIG. 5.

FIG. 6 illustrates an embodiment of a therapy titration module 630 such as is illustrated at 530 in FIG. 5. According to various embodiments, the stimulation control circuit is adapted to set or adjust any one or any combination of stimulation features 631. Examples of stimulation features include the amplitude, frequency, polarity and wave morphology of the stimulation signal. Examples of wave morphology include a square wave, triangle wave, sinusoidal wave, and waves with desired harmonic components to mimic white noise such as is indicative of naturally-occurring baroreflex stimulation. Some embodiments of the stimulation output circuit are adapted to generate a stimulation signal with a predetermined amplitude, morphology, pulse width and polarity, and are further adapted to respond to a control signal from the controller to modify at least one of the amplitude, wave morphology, pulse width and polarity. Some embodiments of the neural stimulation circuitry are adapted to generate a stimulation signal with a predetermined frequency, and are further adapted to respond to a control signal from the controller to modify the frequency of the stimulation signal.

The therapy titration module 630 can be programmed to change stimulation sites 632, such as changing the stimulation electrodes used for a neural target or changing the neural targets for the neural stimulation. For example, different electrodes of a multi-electrode cuff can be used to stimulate a neural target. Examples of neural targets include the right and left vagus nerves, cardiac branches of the vagus nerve, cardiac fats pads, baroreceptors, the carotid sinus, the carotid sinus nerve, and the aortic nerve. Autonomic neural targets can include afferent pathways and efferent pathways and can include sympathetic and parasympathetic nerves. The stimulation can include stimulation to stimulate neural traffic or stimulation to inhibit neural traffic. Thus, stimulation to evoke a sympathetic response can involve sympathetic stimulation and/or parasympathetic inhibition; and stimulation to evoke a parasympathetic response can involve parasympathetic stimulation and/or sympathetic inhibition.

The therapy titration module 630 can be programmed to change stimulation vectors 633. Vectors can include stimulation vectors between electrodes, or stimulation vectors for transducers. For example, the stimulation vector between two electrodes can be reversed. One potential application for reversing stimulation vectors includes changing from stimulating neural activity at the neural target to inhibiting neural activity at the neural target. More complicated combinations of electrodes can be used to provide more potential stimulation vectors between or among electrodes. One potential stimulation vector application involves selective neural stimulation (e.g. selective stimulation of the vagus nerve) or changing between a selective stimulation and a more general stimulation of a nerve trunk.

The therapy titration module 630 can be programmed to control the neural stimulation according to stimulation instructions, such as a stimulation routine or schedule 634, stored in memory. Neural stimulation can be delivered in a stimulation burst, which is a train of stimulation pulses at a predetermined frequency. Stimulation bursts can be characterized by burst durations and burst intervals. A burst duration is the length of time that a burst lasts. A burst interval can be identified by the time between the start of successive bursts. A programmed pattern of bursts can include any combination of burst durations and burst intervals. A simple burst pattern with one burst duration and burst interval can continue periodically for a programmed period or can follow a more complicated schedule. The programmed pattern of bursts can be more complicated, composed of multiple burst durations and burst interval sequences. The programmed pattern of bursts can be characterized by a duty cycle, which refers to a repeating cycle of neural stimulation ON for a fixed time and neural stimulation OFF for a fixed time. Duty cycle is specified by the ON time and the cycle time, and thus can have units of ON time/cycle time. According to some embodiments, the control circuit 528 controls the neural stimulation generated by the stimulation circuitry by initiating each pulse of the stimulation signal. In some embodiments, the stimulation control circuit initiates a stimulation signal pulse train, where the stimulation signal responds to a command from the controller circuitry by generating a train of pulses at a predetermined frequency and burst duration. The predetermined frequency and burst duration of the pulse train can be programmable. The pattern of pulses in the pulse train can be a simple burst pattern with one burst duration and burst interval or can follow a more complicated burst pattern with multiple burst durations and burst intervals. In some embodiments, the stimulation control circuit controls the stimulation output circuit to initiate a neural stimulation session and to terminate the neural stimulation session. The burst duration of the neural stimulation session under the control of the control circuit 528 can be programmable. The controller may also terminate a neural stimulation session in response to an interrupt signal, such as may be generated by one or more sensed parameters or any other condition where it is determined to be desirable to stop neural stimulation.

The illustrated device includes a programmed therapy schedule or routine stored in memory and further includes a clock or timer which can be used to execute the programmable stimulation schedule. For example, a physician can program a daily/weekly schedule of therapy based on the time of day. A stimulation session can begin at a first programmed time, and can end at a second programmed time. Various embodiments initiate and/or terminate a stimulation session based on a signal triggered by a user. Various embodiments use sensed data to enable and/or disable a stimulation session.

According to various embodiments, the stimulation schedule refers to the time intervals or period when the neural stimulation therapy is delivered. A schedule can be defined by a start time and an end time, or a start time and a duration. Various schedules deliver therapy periodically. By way of example and not limitation, a device can be programmed with a therapy schedule to deliver therapy from midnight to 2 AM every day, or to deliver therapy for one hour every six hours, or to deliver therapy for two hours per day, or according to a more complicated timetable. Various device embodiments apply the therapy according to the programmed schedule contingent on enabling conditions, such as sensed exercise periods, patient rest or sleep, low heart rate levels, and the like. For example, the stimulation can be synchronized to the cardiac cycle based on detected events that enable the stimulation. The therapy schedule can also specify how the stimulation is delivered.

Figure 7:
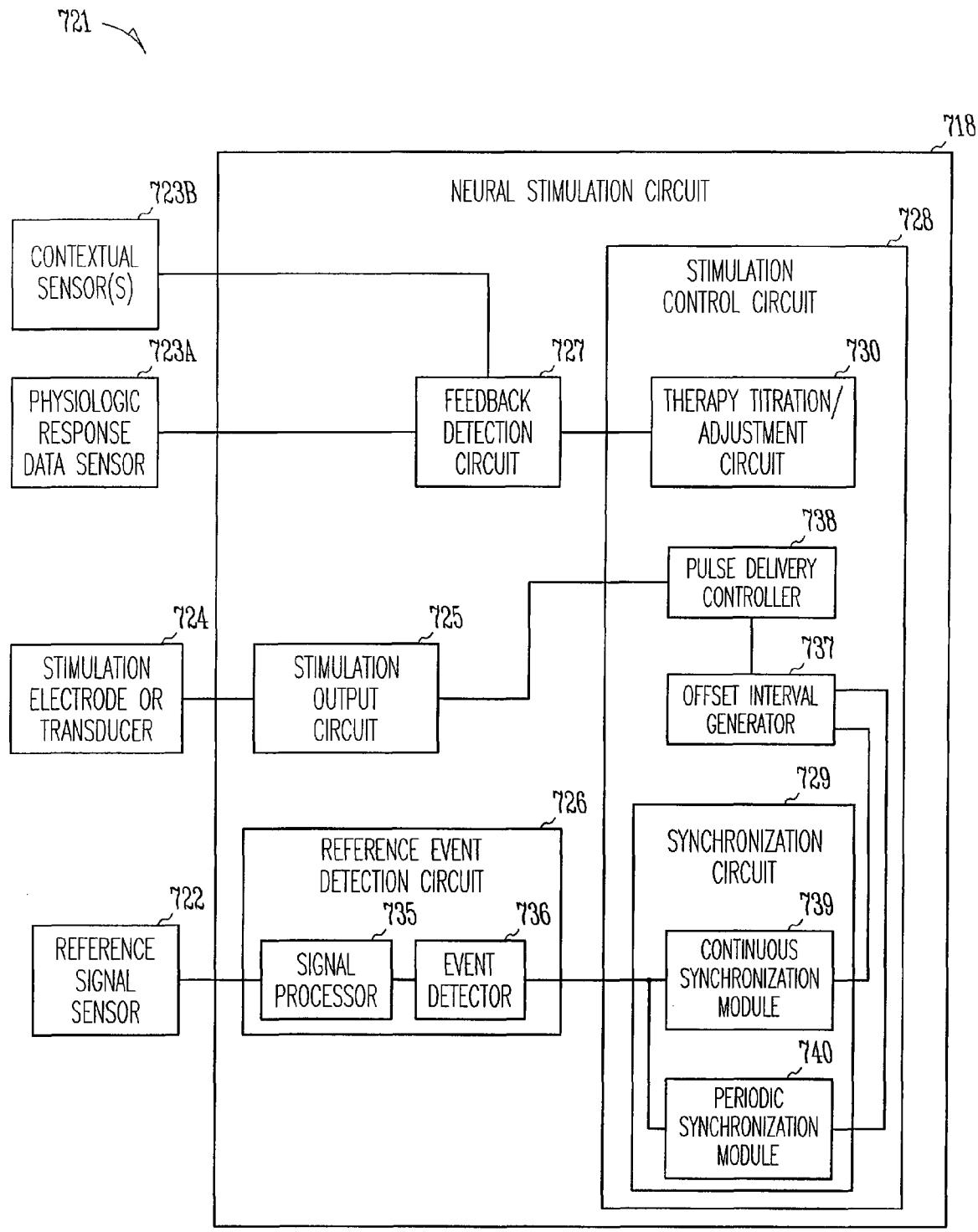
FIG. 7 is a block diagram illustrating an embodiment of a circuit of a neural stimulation system.

FIG. 7 is a block diagram illustrating an embodiment of a circuit of a neural stimulation system 721. The illustrated system 721 includes reference signal sensor 722, a physiologic response data sensor 723A, a stimulation electrode/transducer 724, and a neural stimulation circuit 718. Neural stimulation circuit 718 includes stimulation output circuit 725, a reference event detection circuit 726, a feedback detection circuit 727, and a stimulation control circuit 728.

Reference event detection circuit 726 includes a signal processor 735 and an event detector 736. Signal processor 735 receives the reference signal sensed by reference signal sensor 722 and processes the reference signal in preparation for the detection of the timing reference events by event detector 736. Event detector 736 includes a comparator having an input to receive the processed reference signal, another input to receive a detection threshold, and an output producing a detection signal indicating a detection of the timing reference signal. In one embodiment, signal processor 735 processes the reference signal to extract the timing reference event based on a single cardiac cycle. In one embodiment, signal processor 735 includes a filter having a pass-band corresponding to a frequency range of the timing reference event to prevent unwanted activities in the reference signal from being detected by event detector 736. In an embodiment, signal processor 735 includes a blanking period generator to generate a blanking period that blanks the unwanted activities in the reference signal. This approach is applied when an approximate timing relationship between the timing reference event and the unwanted activities, or an approximate timing relationship between another detectable event and the unwanted activities, is predictable. In an embodiment, the blanking period generator generates a blanking period that blanks cardiac pacing artifacts in the reference signal, i.e., unwanted activities caused by delivery of cardiac pacing pulses. In an embodiment, signal processor 735 includes a timing interval generator to generate a timing interval between an intermediate event and the timing reference event. This approach is applied when the intermediate event is more easily detectable than the timing reference event and when an approximate timing relationship between the intermediate event and the timing reference event is predictable. In an embodiment, signal processor 735 processes the reference signal to provide for extraction of the timing reference event based on a plurality of cardiac cycles. In one embodiment, signal processor 735 includes a signal averaging circuit that averages the reference signal over a predetermined number of cardiac cycles before the detection of the timing reference event by event detector 736.

Stimulation control circuit 728 includes a synchronization circuit 729, a therapy titration circuit 730, an offset interval generator 737, and a pulse delivery controller 738. Synchronization circuit 729 includes one or both of a continuous synchronization module 739 and a periodic synchronization module 740. Continuous synchronization module synchronizes the delivery of the neural stimulation pulses to the timing reference event of consecutive cardiac cycles. Periodic synchronization module synchronizes the delivery of the neural stimulation pulses to the timing reference event of selected cardiac cycles on a periodic basis. Offset interval generator produces an offset interval starting with the detected timing reference event. The pulse delivery controller sends the pulse delivery signal to start a delivery of a burst of a plurality of neural stimulation pulses when the offset interval expires. In one embodiment, the pulse delivery controller sends the pulse delivery signal after the detection of the timing reference event for each of consecutive cardiac cycles. In another embodiment, the pulse delivery controller sends the pulse delivery signal after the detection of the timing reference event for selected cardiac cycles according to a predetermined pattern or schedule, such as on a periodic basis.

The data sensor 723A is used to detect a physiological response to the neural stimulation. In various embodiments, the data sensor 723A is adapted to detect a cardiac response or a non-cardiac response. Examples of cardiac sensors include sensors to sense or detect HRV, HRT, PR interval, T-wave velocity, and action potential duration. Examples of non-cardiac sensors include respiration sensors and blood pressure sensors. A feedback detection circuit 727 is connected to the data sensor to generate a feedback signal based on the sensed data. For example, one embodiment senses an ECG, and extracts a P-wave based on the ECG signal. The therapy titration/adjustment circuit 730 in the stimulation control circuit is responsive to the feedback signal to adjust the therapy (e.g. change signal features, or change stimulation targets, or change stimulation vectors). Contextual sensor(s) or input(s) 723B are also illustrated connected to the feedback detection circuit 727. The feedback detection circuit can provide the neural stimulation feedback signal based on the sensor 723A and the contextual input(s) 723B. Examples of contextual inputs include an activity sensor, a posture sensor and a timer.

Figure 8:
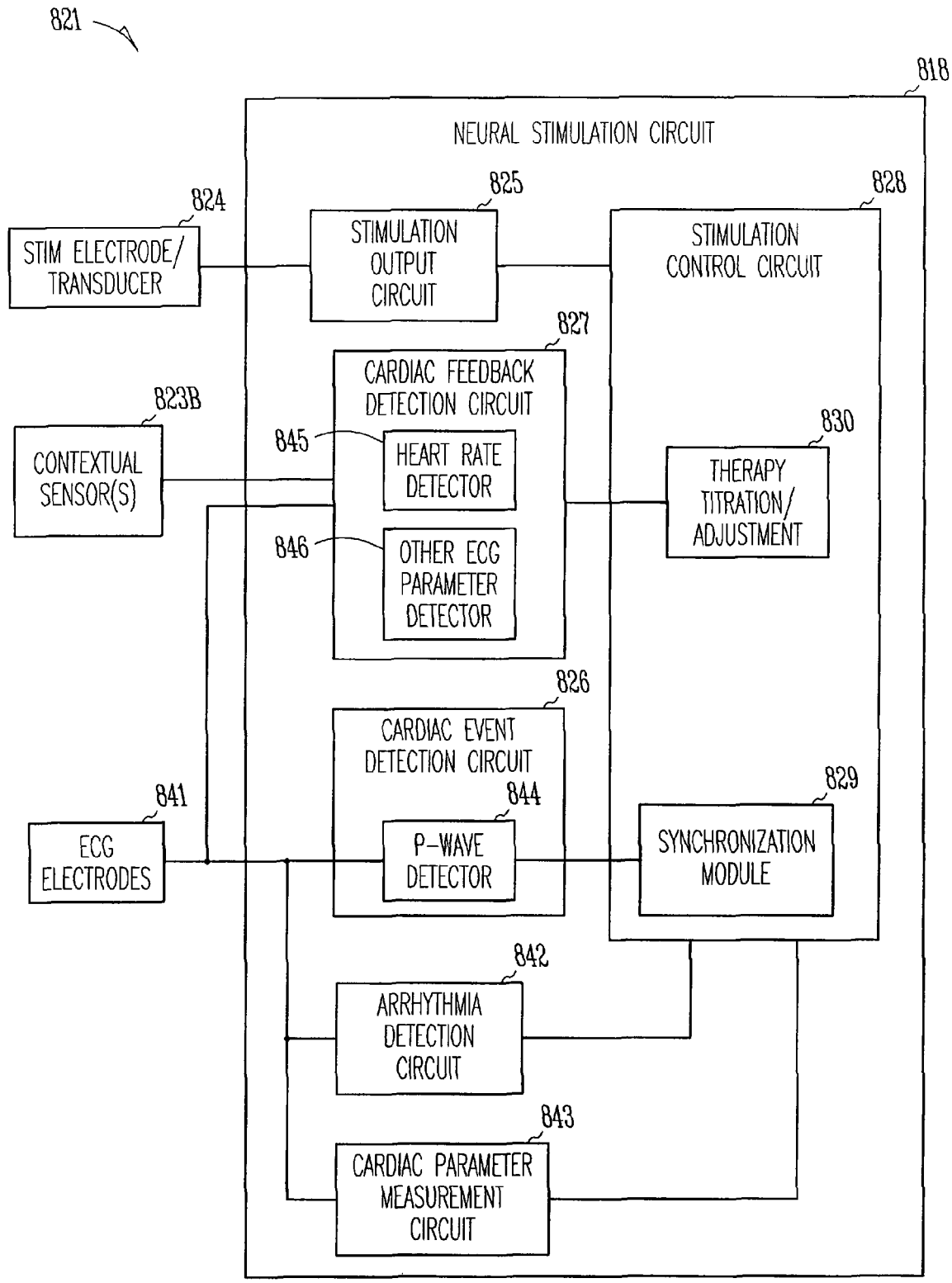
FIG. 8 is a block diagram illustrating an embodiment of a neural stimulation system, which uses a wireless ECG to synchronize neural stimulation to cardiac cycles.

FIG. 8 is a block diagram illustrating an embodiment of a neural stimulation system 821, which uses a wireless ECG to synchronize neural stimulation to cardiac cycles. System 821 includes ECG electrodes 841, stimulation electrode/transducer 824 and a neural stimulation circuit 818. Neural stimulation circuit 818 includes stimulation output circuit 825, a cardiac event detection circuit 826, an arrhythmia detection circuit 842, a cardiac parameter measurement circuit 843, a cardiac feedback detection circuit 827 and a stimulation control circuit 828. Contextual input(s) 823B are also illustrated connected to the feedback detection circuit 827.

In one embodiment, ECG electrodes 841 include surface ECG electrodes. In another embodiment, ECG electrodes 841 include electrodes for sensing a wireless ECG signal. In one embodiment, ECG electrodes 841 include subcutaneous electrodes for sensing a subcutaneous ECG signal. In one embodiment, the subcutaneous electrodes are incorporated onto an implantable medical device, which is to be subcutaneously implanted. In one embodiment, at least one subcutaneous electrode is placed in a selected location in the body near the base of the heart to allow selective detection of atrial depolarizations (P-waves). In an embodiment, multiple subcutaneous electrodes are placed near base and apex of the heart to allow P-wave detection by subtracting out unwanted activities including ventricular depolarizations (R-waves). This approach applies when it is difficult to isolate P-waves by selecting electrode sites and filtering. At least one subcutaneous electrode is placed near the apex of the heart to allow detection of R-waves. The detected R-waves are then used to isolate, by subtraction, P-waves from a subcutaneous ECG signal that includes both P-waves and R-waves.

The signal processor includes a wireless ECG sensing circuit to amplify and filter the subcutaneous ECG signal sensed through ECG electrodes 841. An example of electrodes and a circuit for sensing wireless ECG signals including subcutaneous ECG signals is discussed in U.S. patent application Ser. No. 10/795,126, entitled "WIRELESS ECG IN IMPLANTABLE DEVICES," filed on Mar. 5, 2004, assigned to Cardiac Pacemakers, Inc., which is incorporated herein by reference in its entirety. In one embodiment, the timing reference event is a P-wave, such that cardiac event detection circuit 826 includes a P-wave detector 844 to detect P-waves from the wireless ECG signal. In one specific embodiment, P-wave detector 844 includes a filter having a pass-band corresponding to a frequency range of P-waves. In an embodiment, P-wave detector 844 includes an R-wave detector to detect R-waves from one subcutaneous signal and a blanking period generator to generate blanking periods to blank unwanted activities including the R-waves in another wireless ECG signal. In another specific embodiment, P-wave detector 844 includes an R-wave detector to detect R-waves from the subcutaneous signal and a timing interval generator to generate a timing interval upon detection of each R-wave. A P-wave is estimated to occur at the end of the timing interval. The illustrated cardiac feedback detection circuit 827 includes ECG parameter detectors such as heart rate detector 845 or other ECG parameter detector 846, which is used to provide a feedback signal to the stimulation control circuit. Arrhythmia detection circuit 842 and cardiac parameter measurement circuit 843 provide for other control of neural stimulation based on cardiac conditions. Arrhythmia detection circuit 842 detects one or more types of arrhythmia from the wireless ECG signal. Cardiac parameter measurement module 843 measures one or more cardiac parameters such as a heart rate and an atrioventricular interval from the wireless ECG signal. Neural stimulation may be terminated or enabled, for example, using signals from the arrhythmia detection circuit and the cardiac parameter measurement module.

The illustrated stimulation control circuit 828 includes a synchronization module 829 and a therapy titration/adjustment module 830. Synchronization module 829 synchronizes the delivery of the neural stimulation pulses to the detected cardiac events such as P-waves. In one embodiment, stimulation control circuit 828 includes an offset interval generator and pulse delivery controller. Synchronization circuit 829 can include one or both of a continuous synchronization module to synchronize the delivery of the neural stimulation pulses to the P-wave of each of consecutive cardiac cycles and a periodic synchronization module to synchronize the delivery of the neural stimulation pulses to the P-wave of each of selected cardiac cycles on a periodic basis. The offset interval generator produces an offset interval starting with each detected P-wave. The pulse delivery controller sends the pulse delivery signal to start a delivery of a burst of a plurality of neural stimulation pulses when the offset interval expires. In an embodiment, the pulse delivery controller sends the pulse delivery signal after the detection of the P-wave for each of consecutive cardiac cycles. In an embodiment, the pulse delivery controller sends the pulse delivery signal after the detection of the P-wave for each of selected cardiac cycles according to a predetermined pattern or schedule, such as on a periodic basis. The therapy titration module 830 adjusts the therapy to achieve the desired cardiac activity (e.g. heart rate).

In an embodiment, stimulation control circuit 828 also controls the delivery of the neural stimulation pulses based on the cardiac rhythm detected by arrhythmia detection circuit 842 and/or the cardiac parameters measured by cardiac parameter measurement circuit 843. In one embodiment, stimulation control circuit 828 withholds or adjusts the delivery of the neural stimulation pulses when an arrhythmia is detected. In another embodiment, stimulation control circuit 828 starts, stops, or adjusts the delivery of the neural stimulation pulses based on the measured cardiac parameter, such as the heart rate and the atrioventricular interval.

Figure 9:
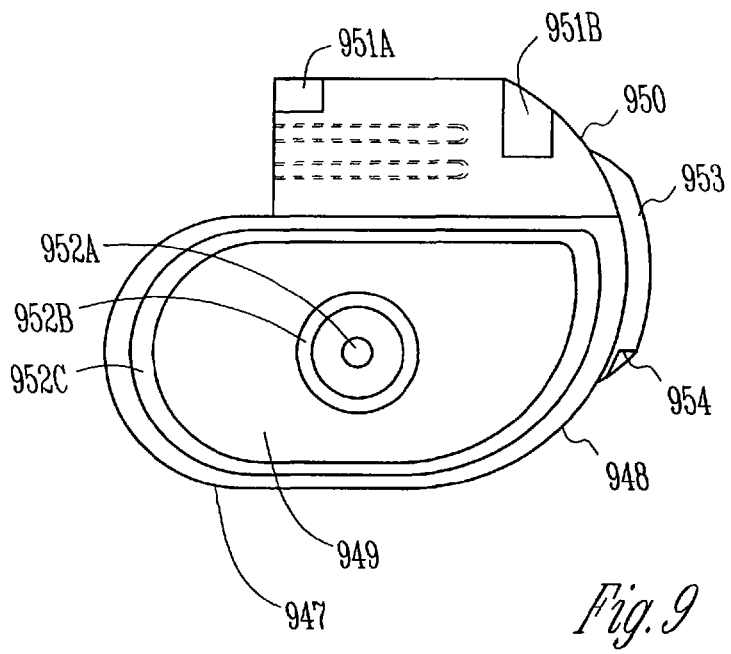
FIG. 9 is an illustration of an embodiment of an electrode system for sensing one or more subcutaneous ECG signals.

FIG. 9 is an illustration of an embodiment of an electrode system for sensing one or more subcutaneous ECG signals. An electrode system for subcutaneous ECG sensing includes two or more implantable electrodes. These implantable electrodes can be selected from the electrodes including, but not being limited to, those illustrated in FIG. 9. The electrodes are selected to allow for sensing electrical activities from a substantial portion of the heart, up to the entire heart. FIG. 9 shows an implantable medical device 947 and electrodes incorporated onto that device. Implantable medical device 947 is to be subcutaneously implanted in a patient in need of neural stimulation to modulate cardiac functions. In an embodiment, one or more of the illustrated electrodes function as ECG electrodes. In another embodiment, in addition to one or more electrodes shown in FIG. 9, ECG electrodes include one or more electrodes electrically connected to implantable medical device 947 through a lead or a satellite wirelessly connected to an IMD.

Implantable medical device 947 includes a hermetically sealed can 948 to house its circuit. Can 948 has an outer surface subject to contact with body tissue. Can 948 includes or provides for a base of a can electrode 949 that is selectable as one of the electrodes for sensing a subcutaneous ECG signal. At least a portion of the outer surface of can 948 is made of electrically conductive material. In one embodiment, can 948 is used as can electrode 949. In an embodiment, can electrode 949 includes at least one conductive portion of can 948. In an embodiment, can electrode 949 is incorporated onto the outer surface of can 948 and is electrically insulated from any conductive portion of can 948 using a non-conductive layer. In an embodiment, a hermetically sealed feedthrough including a conductor provides for an electrical connection between can electrode 949 and the circuit housed in can 948.

A header 950 is attached to can 948 and includes connectors providing for electrical access to the circuit housed in can 948. In one embodiment, one or more of header electrodes 951A-B are incorporated into the header. Header electrodes 951A-B are each selectable as one of the electrodes for sensing a subcutaneous ECG signal.

In one embodiment, two or more concentric electrodes 952A-C are incorporated onto the outer surface of can 948. Each of the concentric electrodes 952A-C is selectable as one of the electrodes for sensing a subcutaneous ECG signal. Concentric electrodes 952A-C are insulated from the conductive portion of can 948 with a non-conductive layer and connected to the circuit housed in can 948 via hermetically sealed feedthroughs. In one embodiment, two electrodes, including an inner electrode and an outer electrode, are selected from concentric electrodes 952A-C for the wireless ECG sensing. In one embodiment, the outer electrode has a ring shape. In an embodiment, the outer electrode has a shape approaching the contour of can 948.

In one embodiment, implantable medical device 947 includes an antenna 953 used for a far-field RF telemetry link providing for communication between implantable medical device 947 and an external system. Antenna 953 is electrically connected to the circuit housed in can 948. In one embodiment, antenna 953 projects from header 950 and extends along one side of can 948. In one embodiment, antenna 953 includes a metal conductor with a distal portion exposed for functioning as an antenna electrode 954, which is selectable as one of the electrodes for sensing a subcutaneous ECG signal.

The electrodes illustrated in FIG. 9 are intended to be examples but not limitations. Other electrode configurations are usable as long as they synchronize the delivery of neural stimulation pulses to cardiac cycles. In various embodiments in which multiple subcutaneous ECG vectors are sensed, multiple pairs of electrodes are selected, simultaneously or one at a time, for a multi-channel (multi-vector) subcutaneous ECG sensing. In an embodiment, one or more of subcutaneous ECG vectors are sensed to approximate one or more vectors of a standard multi-lead surface ECG recording. In an embodiment, multiple subcutaneous ECG vectors are sensed based on needs of specific information for synchronizing the delivery of neural stimulation pulses to cardiac cycles. Such subcutaneous ECG vectors do not necessarily approximate standard surface ECG vectors. In an embodiment, implantable medical device 947 includes header electrodes 951A-B and can electrode 949 for the subcutaneous ECG sensing. Implantable medical device 947 is programmable for sensing subcutaneous ECG vectors between: header electrodes 951A and 951B; header electrode 951A and can electrode 949; and/or header electrode 951B and can electrode 949. In an embodiment, implantable medical device 947 includes one of header electrodes 951A-B, antenna electrode 954, and can electrode 949 for the subcutaneous ECG sensing. Implantable medical device 947 is programmable for sensing subcutaneous ECG vectors between: header electrode 951A or 951B and antenna electrode 954; header electrode 951A or 951B and can electrode 949; and/or antenna electrode 954 and can electrode 949. In an embodiment, implantable medical device 947 includes header electrodes 951A-B, antenna electrode 954, and can electrode 949 for the subcutaneous ECG sensing. Implantable medical device 947 is programmable for sensing subcutaneous ECG vectors between: header electrodes 951A and 954; header electrode 951A and antenna electrode 954; header electrode 951A and can electrode 949; header electrode 951B and antenna electrode 954; header electrode 951B and can electrode 949; and/or antenna electrode 954 and can electrode 949. Other specific embodiments involving any electrode combinations for the subcutaneous ECG sensing will be employed based on needs and consideration for synchronizing the delivery of neural stimulation pulses to cardiac cycles as well as needs and considerations for performing other diagnostic and/or therapeutic functions provided by implantable medical device 947.

The selection of subcutaneous ECG vectors depends on the purpose for the subcutaneous ECG sensing. When the subcutaneous ECG signal is sensed for detecting P-waves, the subcutaneous ECG vector that provide for a reliable P wave detection are selected. When the subcutaneous ECG signal is sensed for detecting R-waves, one or more subcutaneous ECG vectors that provide for a reliable R wave detection are selected. In one embodiment, when more than one subcutaneous ECG vector provides for a reliable sensing for a particular purpose, the subcutaneous ECG vector showing the highest signal-to-noise ratio (SNR) for that purpose is selected. For example, if the subcutaneous ECG is sensed for detecting P waves, the subcutaneous ECG vector showing the highest SNR with P waves being considered as the signal that is selected.

Figure 10:
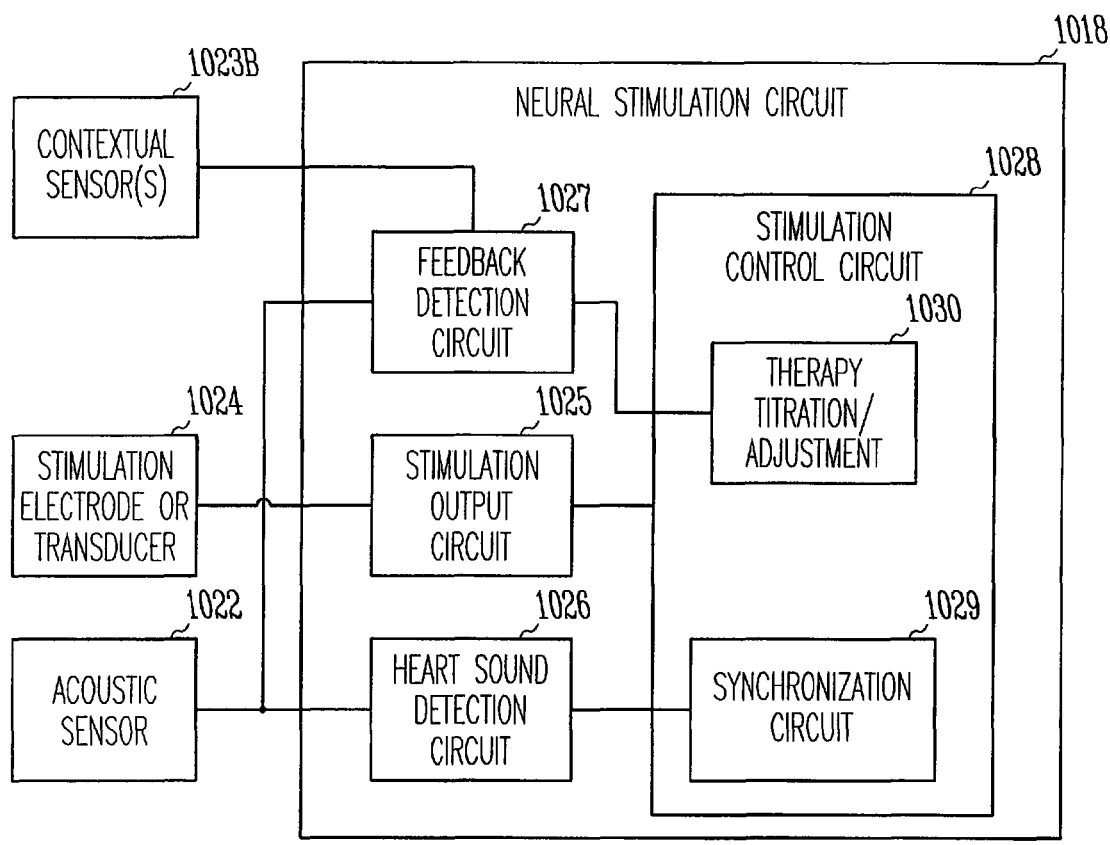
FIG. 10 is a block diagram illustrating an embodiment of a neural stimulation system which uses heart sounds to synchronize neural stimulation to cardiac cycles.

FIG. 10 is a block diagram illustrating an embodiment of a neural stimulation system 1021 which uses heart sounds to synchronize neural stimulation to cardiac cycles. System 1021 includes an acoustic sensor 1022, a stimulation electrode or transducer 1024, and a neural stimulation circuit 1018. Neural stimulation circuit 1018 includes stimulation output circuit 1025, a heart sound detection circuit 1026, feedback detection circuit 1027, and a stimulation control circuit 1028. Contextual sensor(s) or input(s) 1023B are also illustrated connected to the feedback detection circuit 1027.

Acoustic sensor 1022 senses an acoustic signal indicative heart sounds. In one embodiment, acoustic sensor 1022 includes an implantable acoustic sensor. In one embodiment, acoustic sensor 1022 includes an accelerometer. In another embodiment, acoustic sensor 1022 includes a microphone. In an embodiment, acoustic sensor 1022 is included in an implantable medical device. In an embodiment, acoustic sensor 1022 is incorporated onto a lead connected to an implantable medical device.

Heart sound detection circuit 1026 detects predetermined type heart sounds from the acoustic signal. Heart sound detection circuit 1026 includes one or more of a first heart sound (S1) detector to detect S1, a second heart sound (S2) detector to detect S2, a third heart sound (S3) detector to detect S3, and a fourth heart sound (S4) detector to detect S4. In one embodiment, the type of heart sounds to be detected is determined based on whether each particular type of heart sounds is consistently recurring and reliably detectable in an individual patient. In one embodiment, heart sound detection circuit 1026 includes a signal processor and an event detector. In an embodiment, heart sound detection circuit 1026 includes a filter having a pass-band corresponding to a frequency range of the predetermined type heart sounds. In an embodiment, heart sound detection circuit 1026 includes a signal averaging circuit to average the acoustic signal over a predetermined number of cardiac cycles before the detection of the predetermined type heart sounds. In an embodiment, heart sound detection circuit 1026 receives an activity signal indicative of the patient's gross physical activity level and stops detecting heart sounds while the activity signal exceeds a predetermined threshold activity level. In an embodiment, heart sound detection circuit 1026 includes an S2 detector and/or an S3 detector such as those discussed in U.S. patent application Ser. No. 10/746,853, now issued as U.S. Pat. No. 7,431,699, "METHOD AND APPARATUS FOR THIRD HEART SOUND DETECTION," filed on Dec. 24, 2004, assigned to Cardiac Pacemakers, Inc., which is incorporated by reference in its entirety.

S3 is known as an indication of heart failure. A heart failure patient suffers from an abnormal electrical conduction system with excessive conduction delays and deteriorated heart muscles that result in asynchronous and weak heart contraction, and hence, reduced pumping efficiency, or poor hemodynamic performance. While the ECG of a heart failure patient may show excessive delays and/or blockages in portions of the electrical conduction system, S3 indicates his or her heart's abnormal mechanical functions. For example, an increase in S3 activity is known to be an indication of elevated filling pressures, which may result in a state of decompensated heart failure. Additionally, S3 amplitude is also related to filling pressures of the left ventricle during diastole. The pitch, or fundamental frequency, of S3 is related to ventricular stiffness and dimension. Chronic changes in S3 amplitude are correlated to left ventricular chamber stiffness and degree of restrictive filling. Such parameters indicate abnormal cardiac conditions, including degrees of severity, and need of appropriate therapies.

An S3 index (or prevalence) is a ratio of the number of heart beats during which S3 are detected ("S3 beats") to the number of all the heart beats. Because the S3 activity varies throughout the day, the S3 beats are counted for a plurality of measurement sessions distributed over a measurement period. The S3 index is then calculated for the measurement period and trended over multiple measurement periods. A trend of the S3 index provides for an indication of heart failure. For example, an increase in the trend of the S3 index may be indicative of abnormally restrictive filling and elevated filling pressures that lead to edema.

Stimulation control circuit 1028 includes a synchronization module 1029 and a therapy titration/adjustment module 1030. Synchronization module 1029 synchronizes the delivery of the neural stimulation pulses to the predetermined type heart sounds. In one embodiment, stimulation control circuit 1028 includes an offset interval generator and pulse delivery controller. Synchronization circuit can include one or both of a continuous synchronization module to synchronize the delivery of the neural stimulation pulses to the predetermined type heart sound of each of consecutive cardiac cycles and a periodic synchronization module to synchronize the delivery of the neural stimulation pulses to the predetermined type heart sound of each of selected cardiac cycles on a periodic basis. The offset interval generator produces an offset interval starting with the detected predetermined type heart sound. The pulse delivery controller sends the pulse delivery signal to start a delivery of a burst of a plurality of neural stimulation pulses when the offset interval expires. In one embodiment, the pulse delivery controller sends the pulse delivery signal after the detection of the predetermined type heart sound for each of consecutive cardiac cycles. In an embodiment, the pulse delivery controller sends the pulse delivery signal after the detection of the predetermined type heart sound for each of selected cardiac cycles according to a predetermined pattern or schedule, such as on a periodic basis. The therapy titration module 1030 receives a feedback signal from feedback detection circuit 1027. In the illustrated embodiment, the feedback detection circuit generates the feedback signal using acoustic sensor 1022, although other sensed data can be used to provide cardiac activity feedback.

Figure 11:
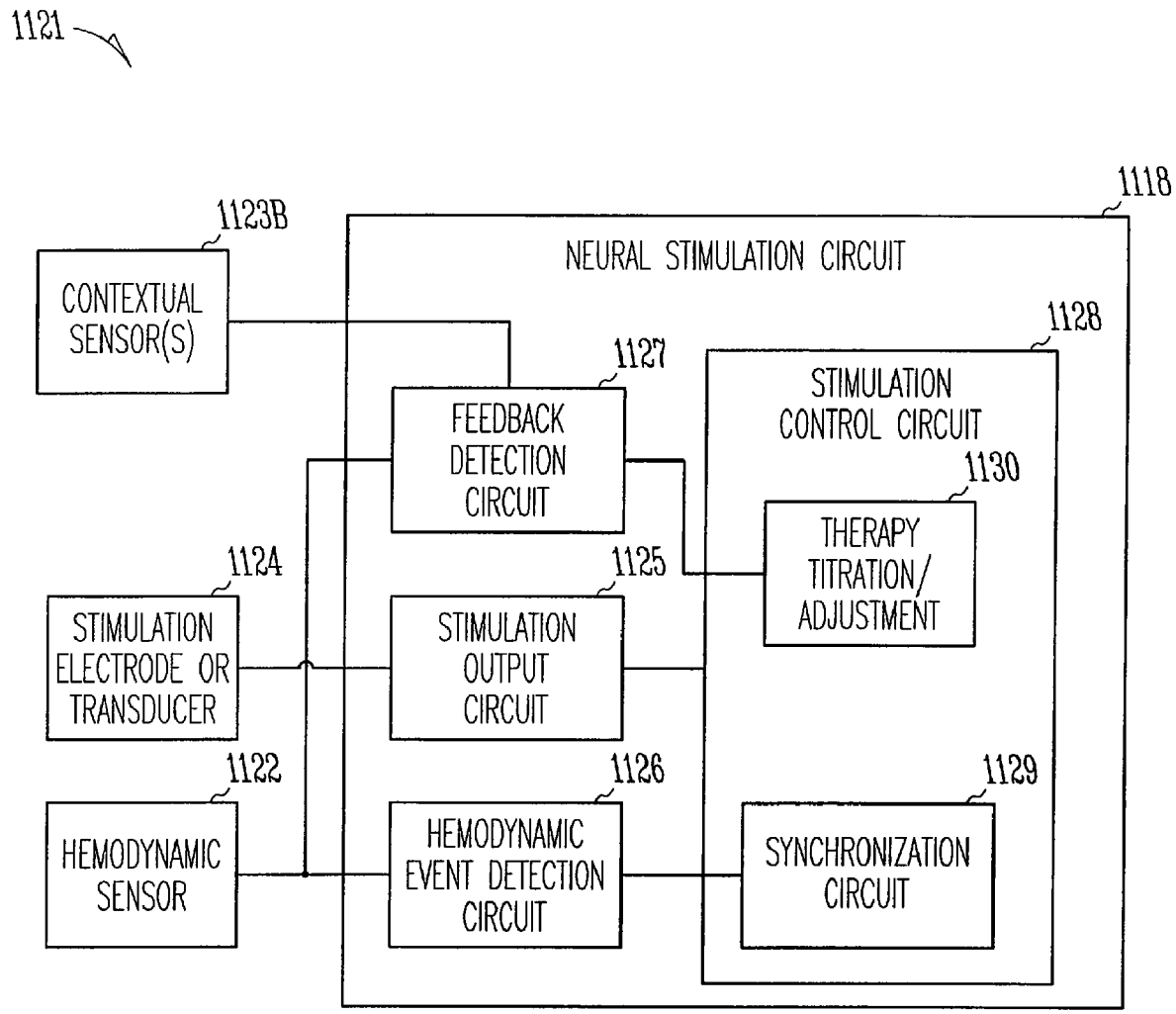
FIG. 11 is a block diagram illustrating an embodiment of a neural stimulation system which uses a hemodynamic signal to synchronize neural stimulation to cardiac cycles.

FIG. 11 is a block diagram illustrating an embodiment of a neural stimulation system 1121, which uses a hemodynamic signal to synchronize neural stimulation to cardiac cycles. System 1121 includes a hemodynamic sensor 1122, a stimulation electrode or transducer 1124, and a neural stimulation circuit 1118. Neural stimulation circuit 1118 includes stimulation output circuit 1125, a hemodynamic event detection circuit 1126, a feedback detection circuit 1127, and a stimulation control circuit 1128. Contextual sensor(s) or input(s) 1123B are also illustrated connected to the feedback detection circuit 1127.

Hemodynamic sensor 1122 senses a hemodynamic signal indicative of hemodynamic performance, such as a signal indicative of blood pressure or flow. In one embodiment, hemodynamic sensor 1122 is an implantable hemodynamic sensor. In one embodiment, hemodynamic sensor 1122 includes a Doppler echocardiographic transducer to sense a peripheral blood flow. In an embodiment, hemodynamic sensor 1122 includes a pressure sensor to sense a central or peripheral blood pressure. In an embodiment, hemodynamic sensor 1122 includes a pulse oximeter to sense an oximetry signal, which is a plethysmographic signal indicative of blood flow. In an embodiment, hemodynamic sensor 1122 includes a thoracic impedance sensor.

Hemodynamic event detection circuit 1126 detects predetermined type hemodynamic events from the hemodynamic signal. The hemodynamic events correspond to a recurring feature of the cardiac cycle that is chosen to be a timing reference to which the neural stimulation is synchronized. In one embodiment, hemodynamic event detection circuit 1126 includes a peak detector that detects predetermined type peaks in the hemodynamic signal. In one embodiment, the peak detector is a pressure peak detector that detects predetermined type peaks in a blood pressure signal. In an embodiment, the peak detector includes a flow peak detector that detects predetermined type peaks in a blood flow signal. The predetermined type peaks are peaks indicative of a characteristic event that occurs during each cardiac cycle. In an embodiment, neural stimulation circuit 1118 includes a derivative calculator to produce a derivative hemodynamic signal by calculating a time derivative of the hemodynamic signal. Hemodynamic event detection circuit 1126 detects the predetermined type hemodynamic event from the derivative hemodynamic signal. In one embodiment, the peak detector detects predetermined type peaks in the derivative hemodynamic signal. In one embodiment, the peak detector is a pressure change peak detector that detects predetermined type peaks in a derivative hemodynamic signal indicative of changes in the blood pressure (e.g., dP/dt). In an embodiment, the peak detector includes a flow change peak detector that detects predetermined type peaks in a derivative hemodynamic signal indicative changes in the blood flow.

The illustrated stimulation control circuit 1128 includes a synchronization module 1129 and a therapy titration module 1130. Synchronization module 1129 synchronizes the delivery of the neural stimulation pulses to the predetermined type hemodynamic events. In one embodiment, stimulation control circuit 1128 includes an offset interval generator and pulse delivery controller. Synchronization circuit 1129 includes one or both of a continuous synchronization module to synchronize the delivery of the neural stimulation pulses to the predetermined type hemodynamic event of each of consecutive cardiac cycles and a periodic synchronization module to synchronize the delivery of the neural stimulation pulses to the predetermined type hemodynamic event of each of selected cardiac cycles on a periodic basis. The offset interval generator produces an offset interval starting with each detected predetermined type hemodynamic event. The pulse delivery controller sends the pulse delivery signal to start a delivery of a burst of a plurality of neural stimulation pulses when the offset interval expires. In one embodiment, the pulse delivery controller sends the pulse delivery signal after the detection of the predetermined type hemodynamic event for each of consecutive cardiac cycles. In an embodiment, the pulse delivery controller sends the pulse delivery signal after the detection of the predetermined type hemodynamic event for each of selected cardiac cycles according to a predetermined pattern or schedule, such as on a periodic basis. The therapy titration module 1130 receives a feedback signal from feedback detection circuit 1127. In the illustrated embodiment, the feedback detection circuit generates the feedback signal using hemodynamic sensor 1122, although other sensed data can be used to provide cardiac activity feedback.

Figure 12:
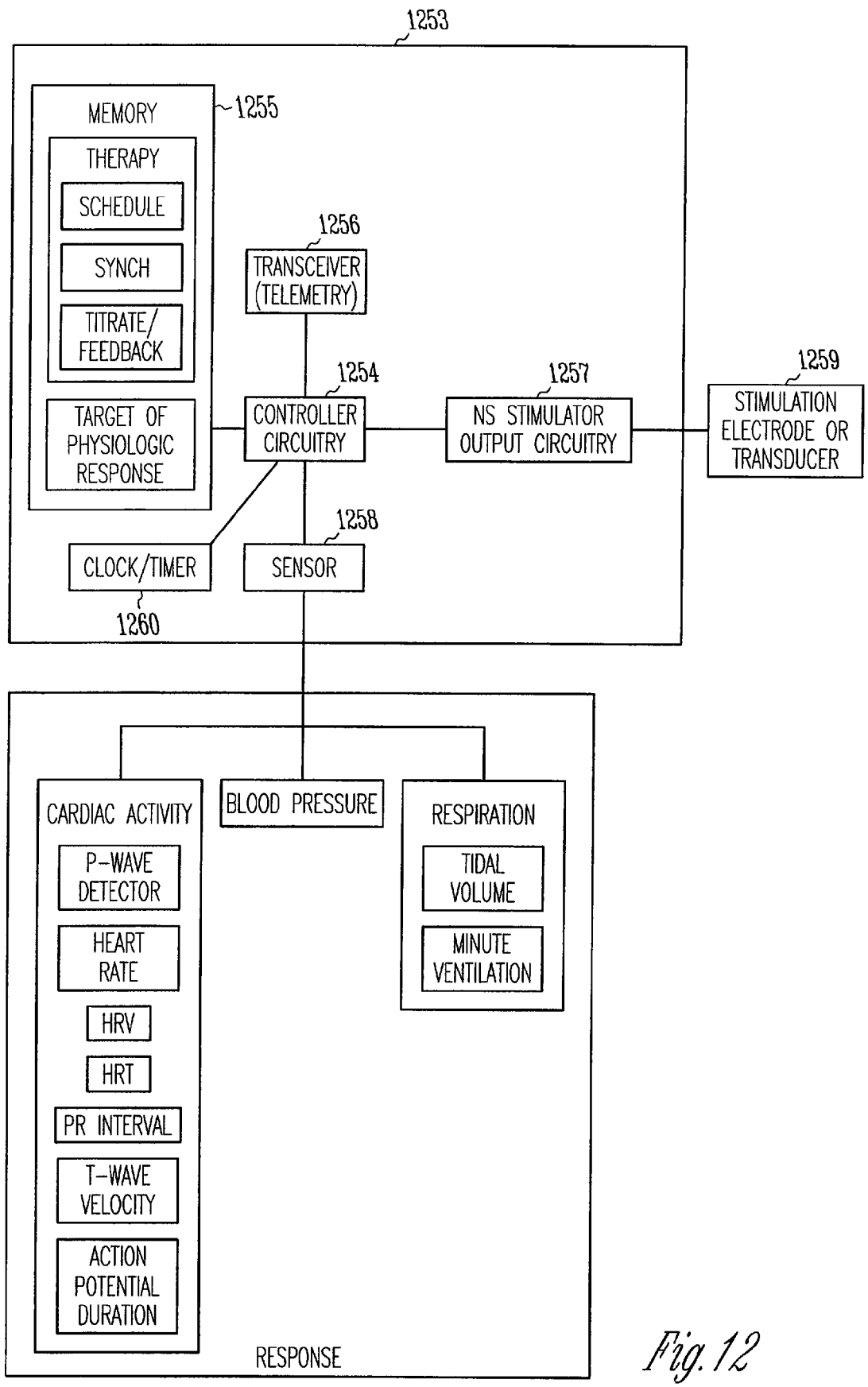
FIG. 12 illustrates an implantable medical device (IMD), according to various embodiments of the present subject matter.

FIG. 12 illustrates an implantable medical device (IMD), according to various embodiments of the present subject matter. The illustrated IMD 1253 provides neural stimulation signals for delivery to predetermined neural targets. The illustrated device includes controller circuitry 1254 and memory 1255. The controller circuitry is capable of being implemented using hardware, software, and combinations of hardware and software. For example, according to various embodiments, the controller circuitry includes a processor to perform instructions embedded in the memory to perform functions associated with the neural stimulation therapy. The illustrated device further includes a transceiver 1256 and associated circuitry for use to communicate with a programmer or another external or internal device. Various embodiments have wireless communication capabilities. For example, some transceiver embodiments use a telemetry coil to wirelessly communicate with a programmer or another external or internal device.

The illustrated device further includes neural stimulation output circuitry 1257 and sensor circuitry 1258. According to some embodiments, one or more leads are able to be connected to the sensor circuitry and neural stimulation circuitry. Some embodiments use wireless connections between the sensor(s) and sensor circuitry, and some embodiments use wireless connections between the stimulator circuitry and electrodes. According to various embodiments, the neural stimulation circuitry is used to apply electrical stimulation pulses to desired neural targets, such as through one or more stimulation electrodes 1259 positioned at predetermined location(s). Some embodiments use transducers to provide other types of energy, such as ultrasound, light or magnetic energy. In various embodiments, the sensor circuitry is used to detect physiological responses. Examples of physiological responses include cardiac activity such as heart rate, HRV, PR interval, T-wave velocity, and action potential duration. Other examples of physiological responses include hemodynamic responses such as blood pressure, and respiratory responses such as tidal volume and minute ventilation. The controller circuitry can control the therapy provided by system using a therapy schedule and a therapy titration routine in memory 1255, or can compare a target range (or ranges) of the sensed physiological response(s) stored in the memory 1255 to the sensed physiological response(s) to appropriately adjust the intensity of the neural stimulation/inhibition.

Some embodiments are adapted to change a stimulation signal feature, the neural stimulation target and/or change the neural stimulation vector as part of a neural stimulation titration routine. According to various embodiments using neural stimulation, the stimulation output circuitry 1257 is adapted to set or adjust any one or any combination of stimulation features based on commands from the controller 1254. Examples of stimulation features include the amplitude, frequency, polarity and wave morphology of the stimulation signal. Examples of wave morphology include a square wave, triangle wave, sinusoidal wave, and waves with desired harmonic components to mimic white noise such as is indicative of naturally-occurring baroreflex stimulation. Some embodiments are adapted to generate a stimulation signal with a predetermined amplitude, morphology, pulse width and polarity, and are further adapted to respond to a control signal from the controller to modify at least one of the amplitude, wave morphology, pulse width and polarity. Some embodiments are adapted to generate a stimulation signal with a predetermined frequency, and are further adapted to respond to a control signal from the controller to modify the frequency of the stimulation signal.

The controller 1254 can be programmed to control the neural stimulation delivered by the stimulation output circuitry 1257 according to stimulation instructions, such as a stimulation schedule, stored in the memory 1255. Neural stimulation can be delivered in a stimulation burst, which is a train of stimulation pulses at a predetermined frequency. Stimulation bursts can be characterized by burst durations and burst intervals. A burst duration is the length of time that a burst lasts. A burst interval can be identified by the time between the start of successive bursts. A programmed pattern of bursts can include any combination of burst durations and burst intervals. A simple burst pattern with one burst duration and burst interval can continue periodically for a programmed period or can follow a more complicated schedule. The programmed pattern of bursts can be more complicated, composed of multiple burst durations and burst interval sequences. The programmed pattern of bursts can be characterized by a duty cycle, which refers to a repeating cycle of neural stimulation ON for a fixed time and neural stimulation OFF for a fixed time.

According to some embodiments, the controller 1254 controls the neural stimulation generated by the stimulation circuitry by initiating each pulse of the stimulation signal. In some embodiments, the controller circuitry initiates a stimulation signal pulse train, where the stimulation signal responds to a command from the controller circuitry by generating a train of pulses at a predetermined frequency and burst duration. The predetermined frequency and burst duration of the pulse train can be programmable. The pattern of pulses in the pulse train can be a simple burst pattern with one burst duration and burst interval or can follow a more complicated burst pattern with multiple burst durations and burst intervals. In some embodiments, the controller 1254 controls the stimulator output circuitry 1257 to initiate a neural stimulation session and to terminate the neural stimulation session. The burst duration of the neural stimulation session under the control of the controller 1254 can be programmable. The controller may also terminate a neural stimulation session in response to an interrupt signal, such as may be generated by one or more sensed parameters or any other condition where it is determined to be desirable to stop neural stimulation.

The sensor circuitry is used to detect a physiological response. The detected response can be cardiac activity or surrogates of cardiac activity such as blood pressure and respiration measurements. Examples of cardiac activity include a P-wave and heart rate. The controller 1254 compares the response to a target range stored in memory, and controls the neural stimulation based on the comparison in an attempt to keep the response within the target range. The target range can be programmable.

The illustrated device includes a clock or timer 1260 which can be used to execute the programmable stimulation schedule. For example, a physician can program a daily schedule of therapy based on the time of day. The therapy can be delivered in synchrony with cardiac activity (synch routine in memory 1255) and with cardiac activity feedback (titrate/feedback routine in memory 1255). A stimulation session can begin at a first programmed time, and can end at a second programmed time. Various embodiments initiate and/or terminate a stimulation session based on a signal triggered by a user. Various embodiments use sensed data to enable and/or disable a stimulation session.

The illustrated memory includes a schedule. According to various embodiments, the schedule refers to the time intervals or period when the neural stimulation therapy is delivered. A schedule can be defined by a start time and an end time, or a start time and a duration. Various schedules deliver therapy periodically. According to various examples, a device can be programmed with a therapy schedule to deliver therapy from midnight to 2 AM every day, or to deliver therapy for one hour every six hours, or to delivery therapy for two hours per day, or according to a more complicated timetable. Various device embodiments apply the therapy according to the programmed schedule contingent on enabling conditions, such as poor glucose control, patient rest or sleep, low heart rate levels, and the like. The illustrated memory includes a synchronization routine and a titration feedback routine, which are used by the control to control the timing and adjustments of neural stimulation generated by the neural stimulator output circuitry.

Figure 13:
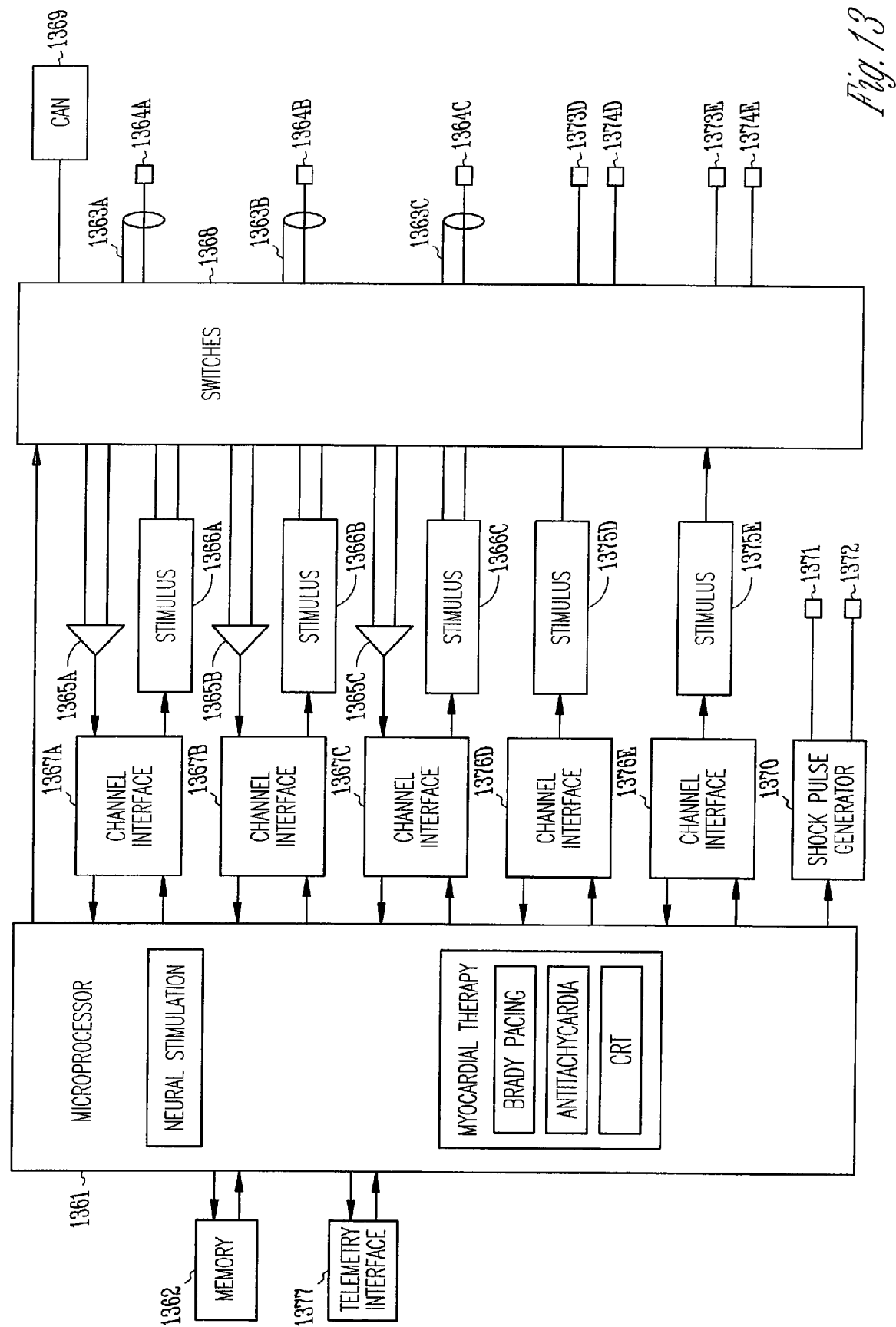
FIG. 13 shows a system diagram of an embodiment of a microprocessor-based implantable device, according to various embodiments.

FIG. 13 shows a system diagram of an embodiment of a microprocessor-based implantable device, according to various embodiments. The controller of the device is a microprocessor 1361 which communicates with a memory 1362 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 1363A-C and tip electrodes 1364A-C, sensing amplifiers 1365A-C, pulse generators 1366A-C, and channel interfaces 1367A-C. Each channel thus includes a pacing channel made up of the pulse generator connected to the electrode and a sensing channel made up of the sense amplifier connected to the electrode. The channel interfaces communicate bidirectionally with the microprocessor, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias. The sensing of these channels can be used to detect cardiac activity for use in synchronizing neural stimulation and for use as feedback in titrating the neural stimulation.

The electrodes of each bipolar lead are connected via conductors within the lead to a switching network 1368 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 1369 or an electrode on another lead serving as a ground electrode. A shock pulse generator 1370 is also interfaced to the controller for delivering a defibrillation shock via a pair of shock electrodes 1371 and 1372 to the atria or ventricles upon detection of a shockable tachyarrhythmia.

Neural stimulation channels, identified as channels D and E, are incorporated into the device for delivering parasympathetic stimulation and/or sympathetic inhibition, where one channel includes a bipolar lead with a first electrode 1373D and a second electrode 1374D, a pulse generator 1375D, and a channel interface 1376D, and the other channel includes a bipolar lead with a first electrode 1373E and a second electrode 1374E, a pulse generator 1375E, and a channel interface 1376E. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, and the like. In this embodiment, each of the neural stimulation channels uses a lead which can be intravascularly disposed near an appropriate neural target. Other types of leads and/or electrodes may also be employed. A nerve cuff electrode may be used in place of an intravascularly disposed electrode to provide neural stimulation. In some embodiments, the leads of the neural stimulation electrodes are replaced by wireless links.

The figure illustrates a telemetry interface 1377 connected to the microprocessor, which can be used to communicate with an external device. The illustrated microprocessor is capable of performing neural stimulation therapy routines and myocardial (CRM) stimulation routines. The neural stimulation routines can target nerves to affect cardiac activity (e.g. heart rate and contractility). Examples of myocardial therapy routines include bradycardia pacing therapies, anti-tachycardia shock therapies such as cardioversion or defibrillation therapies, anti-tachycardia pacing therapies (ATP), and cardiac resynchronization therapies (CRT).

Figure 14:
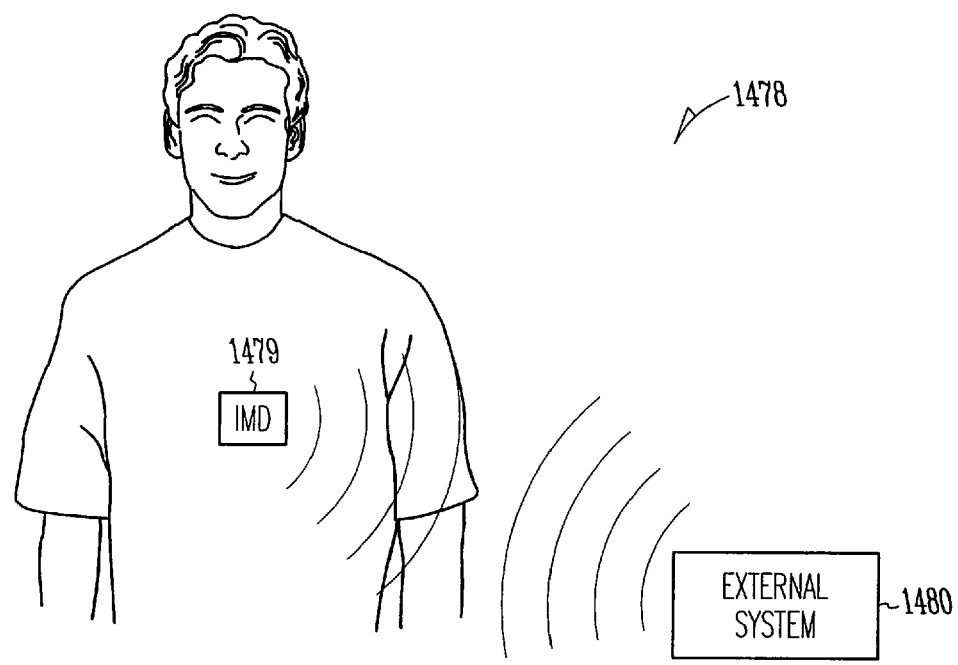
FIG. 14 illustrates a system including an implantable medical device (IMD) and an external system or device, according to various embodiments of the present subject matter.

FIG. 14 illustrates a system 1478 including an implantable medical device (IMD) 1479 and an external system or device 1480, according to various embodiments of the present subject matter. Various embodiments of the IMD include a combination of NS and CRM functions. The IMD may also deliver biological agents and pharmaceutical agents. The external system and the IMD are capable of wirelessly communicating data and instructions. In various embodiments, for example, the external system and IMD use telemetry coils to wirelessly communicate data and instructions. Thus, the programmer can be used to adjust the programmed therapy provided by the IMD, and the IMD can report device data (such as battery and lead resistance) and therapy data (such as sense and stimulation data) to the programmer using radio telemetry, for example. According to various embodiments, the IMD stimulates/inhibits a neural target to affect cardiac activity.

The external system allows a user such as a physician or other caregiver or a patient to control the operation of the IMD and obtain information acquired by the IMD. In one embodiment, external system includes a programmer communicating with the IMD bi-directionally via a telemetry link. In another embodiment, the external system is a patient management system including an external device communicating with a remote device through a telecommunication network. The external device is within the vicinity of the IMD and communicates with the IMD bi-directionally via a telemetry link. The remote device allows the user to monitor and treat a patient from a distant location. The patient monitoring system is further discussed below.

The telemetry link provides for data transmission from implantable medical device to external system. This includes, for example, transmitting real-time physiological data acquired by IMD, extracting physiological data acquired by and stored in IMD, extracting therapy history data stored in implantable medical device, and extracting data indicating an operational status of the IMD (e.g., battery status and lead impedance). Telemetry link also provides for data transmission from external system to IMD. This includes, for example, programming the IMD to acquire physiological data, programming IMD to perform at least one self-diagnostic test (such as for a device operational status), and programming the IMD to deliver at least one therapy.

Figure 15:
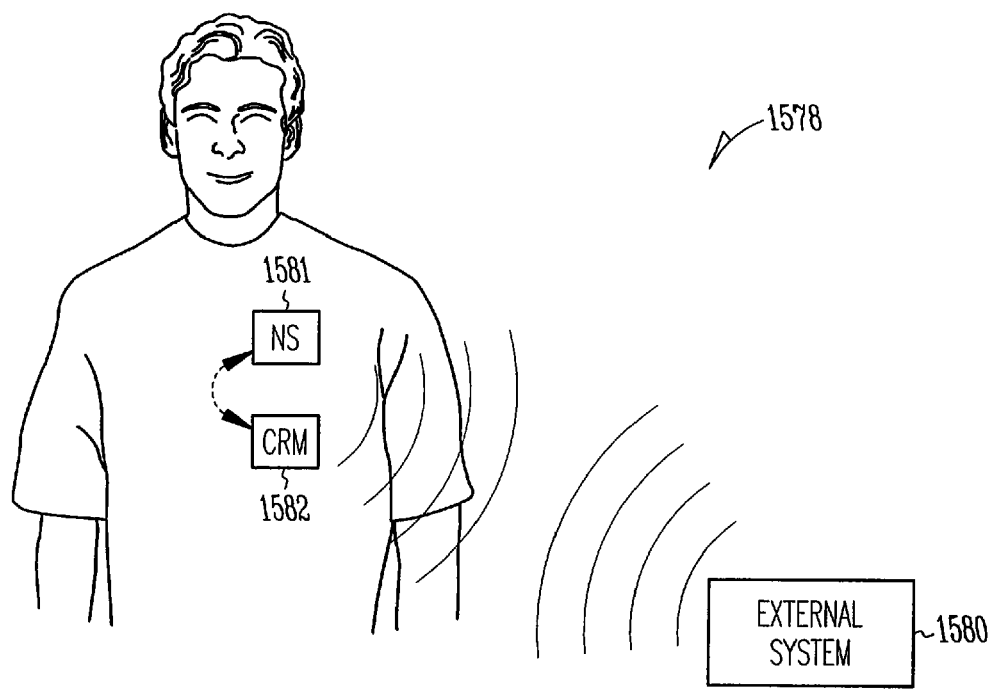
FIG. 15 illustrates a system including an external device, an implantable neural stimulator (NS) device and an implantable cardiac rhythm management (CRM) device, according to various embodiments of the present subject matter.

FIG. 15 illustrates a system 1578 including an external device 1580, an implantable neural stimulator (NS) device 1581 and an implantable cardiac rhythm management (CRM) device 1582, according to various embodiments of the present subject matter. Various aspects involve a method for communicating between an NS device and a CRM device or other cardiac stimulator. In various embodiments, this communication allows one of the devices 1581 or 1582 to deliver more appropriate therapy (i.e. more appropriate NS therapy or CRM therapy) based on data received from the other device. Some embodiments provide on-demand communications. In various embodiments, this communication allows each of the devices to deliver more appropriate therapy (i.e. more appropriate NS therapy and CRM therapy) based on data received from the other device. For example, ECG data from the CRM device can be communicated to the NS device for use in synchronizing and titrating the neural stimulation. The illustrated NS device and the CRM device are capable of wirelessly communicating with each other, and the external system is capable of wirelessly communicating with at least one of the NS and the CRM devices. For example, various embodiments use telemetry coils to wirelessly communicate data and instructions to each other. In other embodiments, communication of data and/or energy is by ultrasonic means. Rather than providing wireless communication between the NS and CRM devices, various embodiments provide a communication cable or wire, such as an intravenously-fed lead, for use to communicate between the NS device and the CRM device. In some embodiments, the external system functions as a communication bridge between the NS and CRM devices.

Figure 16:
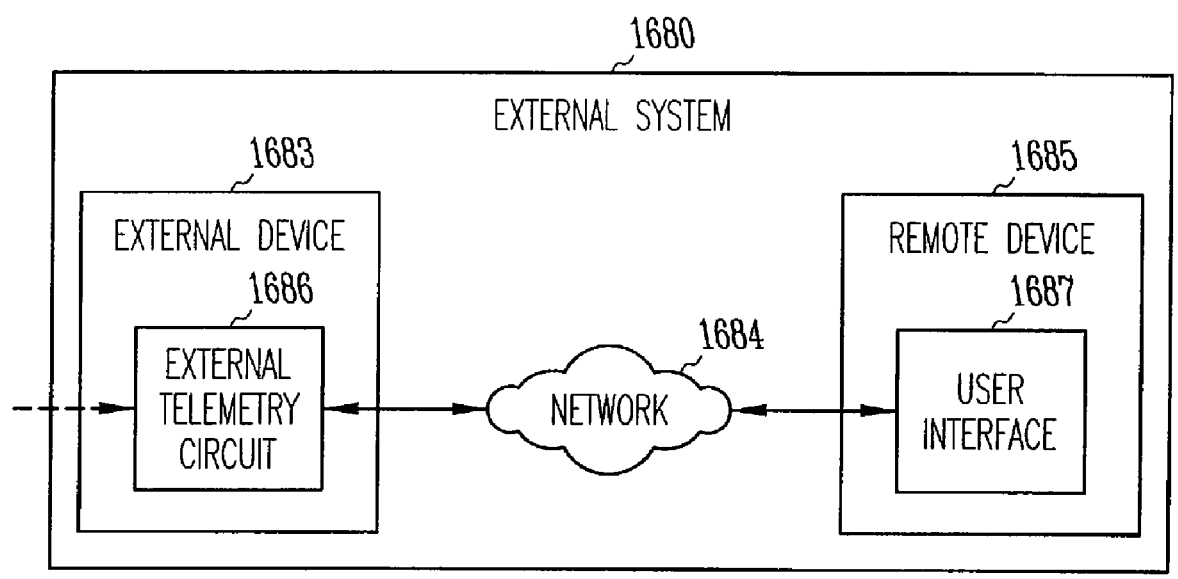
FIG. 16 is a block diagram illustrating an embodiment of an external system.

FIG. 16 is a block diagram illustrating an embodiment of an external system 1680. The external system includes a programmer, in some embodiments. In the illustrated embodiment, the external system includes a patient management system. As illustrated, the external system 1680 is a patient management system including an external device 1683, a telecommunication network 1684, and a remote device 1685. External device 1683 is placed within the vicinity of an IMD and includes external telemetry system 1686 to communicate with the IMD. Remote device(s) 1685 is in one or more remote locations and communicates with external device 1683 through network 1684, thus allowing a physician or other caregiver to monitor and treat a patient from a distant location and/or allowing access to various treatment resources from the one or more remote locations. The illustrated remote device includes a user interface 1687.

Figure 17:
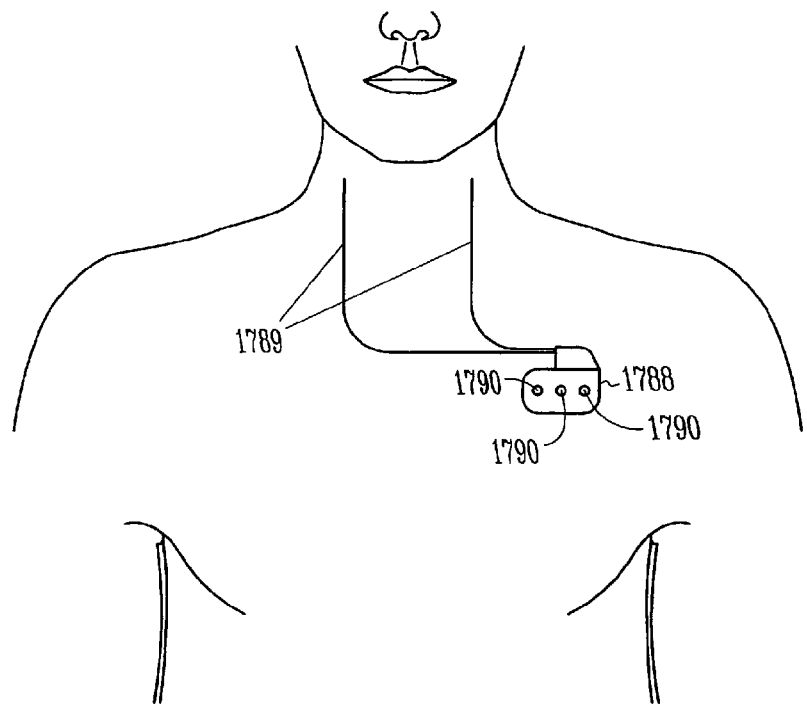
FIG. 17 illustrates a system embodiment in which an IMD is placed subcutaneously or submuscularly in a patient's chest with lead(s) positioned to stimulate a vagus nerve.

FIG. 17 illustrates a system embodiment in which an IMD 1788 is placed subcutaneously or submuscularly in a patient's chest with lead(s) 1789 positioned to stimulate a vagus nerve. According to various embodiments, neural stimulation lead (s) 1789 are subcutaneously tunneled to a neural target, and can have a nerve cuff electrode to stimulate the neural target. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein. Other embodiments deliver neural stimulation to the neural target from within the trachea, the laryngeal branches of the internal jugular vein, and the subclavian vein. The neural targets can be stimulated using other energy waveforms, such as ultrasound and light energy waveforms. Other neural targets can be stimulated, such as cardiac nerves and cardiac fat pads. The illustrated system includes leadless ECG electrodes on the housing of the device. These ECG electrodes 1790 are capable of being used to detect heart rate, for example. Various embodiments include lead(s) positioned to provide a CRM therapy to a heart, and with lead(s) positioned to stimulate and/or inhibit neural traffic at a neural target, such as a vagus nerve, according to various embodiments.

Figure 18:
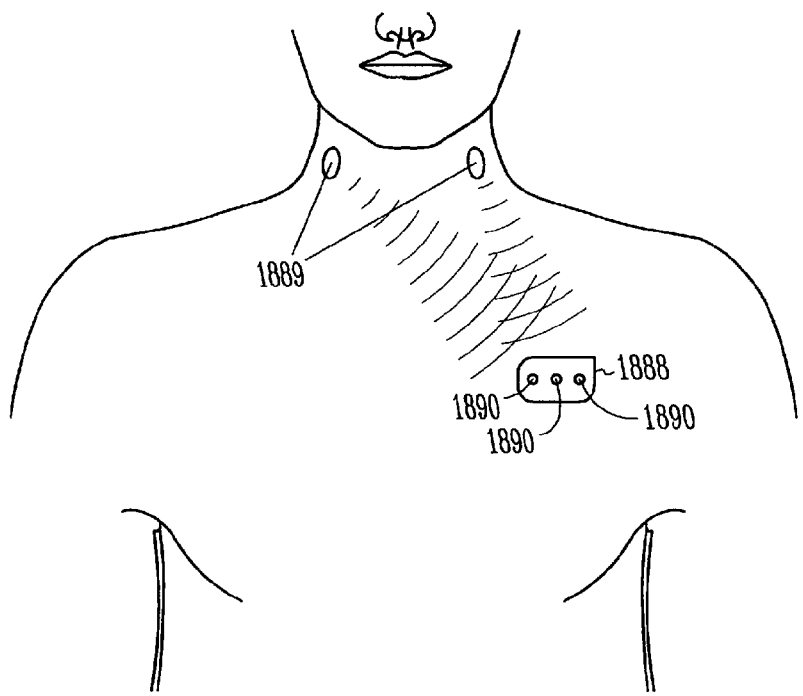
FIG. 18 illustrates a system embodiment that includes an implantable medical device (IMD) with satellite electrode(s) positioned to stimulate at least one neural target.

FIG. 18 illustrates a system embodiment that includes an implantable medical device (IMD) 1888 with satellite electrode(s) 1889 positioned to stimulate at least one neural target. The satellite electrode(s) are connected to the IMD, which functions as the planet for the satellites, via a wireless link. Stimulation and communication can be performed through the wireless link. Examples of wireless links include RF links and ultrasound links. Examples of satellite electrodes include subcutaneous electrodes, nerve cuff electrodes and intravascular electrodes. Various embodiments include satellite neural stimulation transducers used to generate neural stimulation waveforms such as ultrasound and light waveforms. The illustrated system includes leadless ECG electrodes on the housing of the device. These ECG electrodes 1890 are capable of being used to detect heart rate, for example. Various embodiments include lead(s) positioned to provide a CRM therapy to a heart, and with satellite transducers positioned to stimulate/inhibit a neural target such as a vagus nerve, according to various embodiments.

One of ordinary skill in the art will understand that the modules and other circuitry shown and described herein can be implemented using software, hardware, and combinations of software and hardware. As such, the term module is intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter.

The above-identified embodiments, and portions of the illustrated embodiments, are not necessarily mutually exclusive. These embodiments, or portions there of, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A system, comprising:
   a reference event detection circuit configured to receive an input from a reference signal sensor and generate a synchronization control signal using a detected cardiac activity event;
   a feedback detection circuit configured to receive an input from at least one feedback sensor and generate a feedback control signal, wherein the at least one feedback sensor is configured to sense cardiac activity including heart rate, and;
   a stimulation control circuit configured to generate a stimulation control signal, the stimulation control circuit including a synchronization circuit responsive to the synchronization control signal to time the stimulation control signal, the stimulation control circuit further including a therapy titration circuit responsive to the feedback control signal to adjust the stimulation control signal; and
   a stimulation output circuit responsive to the stimulation control signal from the stimulation control circuit and configured to generate a neural stimulation signal for use in stimulating at least one autonomic neural target,
   wherein the stimulation control circuit is configured to receive sensed heart rate from the feedback detection circuit before controlling the stimulation output circuit to generate the neural stimulation signal, to control the stimulation output circuit to generate the neural stimulation signal, and to titrate the neural stimulation signal to maintain heart rate, and
   wherein the stimulation control circuit is configured to change a stimulation vector to maintain heart rate.

2. The system of claim 1, wherein the autonomic neural target includes a neural target that affects heart rate.

3. The system of claim 1, wherein the autonomic neural target includes a neural target that affects a P-R interval, a neural target that affects blood pressure, a neural target that affects heart rate variability (HRV), a neural target that affects heart rate turbulence (HRT), a QT interval or atrial/ventricular refractory periods.

4. The system of claim 1, wherein the stimulation control circuit is adapted to generate the neural stimulation signal for use by at least one electrode in electrically stimulating the autonomic neural target.

5. The system of claim 1, wherein the stimulation control circuit is adapted to generate the neural stimulation signal for use by at least one transducer in stimulating the autonomic neural target using non-electrical stimulation energy.

6. The system of claim 1, wherein the stimulation control circuit includes an offset interval generator for use in offsetting the stimulation control signal from the synchronization control signal.

7. The system of claim 1, wherein the reference event detection circuit includes a P-wave detector.

8. The system of claim 1, wherein a sensor functions as the reference sensor and the feedback sensor.

9. The system of claim 1, wherein the feedback detection circuit is adapted to receive a contextual input and generate the feedback control signal using the contextual input and the sensor.

10. The system of claim 9, wherein the contextual input includes a posture sensor, an activity sensor, or both the posture sensor and the activity sensor.

11. The system of claim 9, wherein the contextual input includes a timer.

12. The system of claim 1, wherein the at least one feedback sensor includes a heart rate variability (HRV) sensor.

13. The system of claim 1, wherein the at least one feedback sensor includes a heart rate turbulence (HRT) sensor.

14. The system of claim 1, wherein the at least one feedback sensor includes a PR interval sensor.

15. The system of claim 1, wherein the at least one feedback sensor includes a T-wave velocity sensor.

16. The system of claim 1, wherein the at least one feedback sensor includes an action potential duration sensor.

17. The system of claim 1, wherein the at least one feedback sensor includes a non-cardiac data sensor.

18. The system of claim 17, wherein the non-cardiac data sensor includes a respiration sensor.

19. The system of claim 17, wherein the non-cardiac data sensor includes a blood pressure sensor.

20. The system of claim 1, wherein the at least one feedback sensor includes a sensor adapted to detect heart sounds.

21. The system of claim 20, wherein the detected heart sounds include a ventricular diastolic filling sound indicative of a pathological condition, and the stimulation control circuit is configured to use the ventricular diastolic filling sound indicative of a pathological condition as feedback to control the neural stimulation signal.

22. The system of claim 21, wherein the detected heart sounds include the third heart sound (S3) indicative of heart failure, and the stimulation control circuit is configured to use S3 indicative of heart failure as feedback to control the neural stimulation signal.

23. The system of claim 22, wherein the stimulation control circuit is configured to calculate an S3 index for a measurement period, to trend the S3 index over multiple measurement periods, and use the trend of the S3 index as an indicator of heart failure.

24. The system of claim 1, wherein the stimulation control circuit is configured to change a stimulation site to maintain heart rate.

25. The system of claim 1, wherein the stimulation control circuit is configured to change a stimulation routine or schedule to maintain heart rate.

26. A system, comprising:
   a reference event detection circuit configured to receive an input from a reference signal sensor and generate a synchronization control signal using a detected cardiac activity event;
   a feedback detection circuit configured to receive an input from a feedback sensor and generate a feedback control signal, wherein the feedback sensor includes a sensor adapted to detect heart sounds and is configured to sense cardiac activity including heart rate;
   a stimulation control circuit configured to generate a stimulation control signal, the stimulation control circuit including a synchronization circuit responsive to the synchronization control signal to time the stimulation control signal, the stimulation control circuit further including a therapy titration circuit responsive to the feedback control signal to use detected heart sounds as feedback for adjusting the stimulation control signal; and
   a stimulation output circuit responsive to the stimulation control signal from the stimulation control circuit and configured to generate a neural stimulation signal for use in stimulating at least one autonomic neural target,
   wherein the stimulation control circuit is configured to change a stimulation vector to maintain heart rate.

27. The system of claim 26, wherein the detected heart sounds include a ventricular diastolic filling sound indicative of a pathological condition, and the stimulation control circuit is configured to use the ventricular diastolic filling sound indicative of a pathological condition as feedback to control the neural stimulation signal.

28. The system of claim 27, wherein the detected heart sounds include the third heart sound (S3) indicative of heart failure, and the stimulation control circuit is configured to use S3 indicative of heart failure as feedback to control the neural stimulation signal.

29. The system of claim 28, wherein the stimulation control circuit is configured to calculate an S3 index for a measurement period, to trend the S3 index over multiple measurement periods, and use the trend of the S3 index as an indicator of heart failure.

* * * * *